United States Patent [19]

Umeda et al.

[11] Patent Number: 5,673,260
[45] Date of Patent: Sep. 30, 1997

[54] METHOD AND SYSTEM FOR CDMA MOBILE COMMUNICATION

[75] Inventors: Narumi Umeda, Yokohamashi; Akihiro Higashi; Akira Hiroike, both of Yokosukashi; Akira Kaiyama, Yokohamashi, all of Japan

[73] Assignee: NTT Mobile Communications Network Inc., Tokyo, Japan

[21] Appl. No.: 530,186

[22] PCT Filed: Feb. 9, 1995

[86] PCT No.: PCT/JP95/00181

§ 371 Date: Oct. 5, 1995

§ 102(e) Date: Oct. 5, 1995

[87] PCT Pub. No.: WO95/22213

PCT Pub. Date: Aug. 17, 1995

[30] Foreign Application Priority Data

| Feb. 9, 1994 | [JP] | Japan | 6-015133 |
| May 9, 1994 | [JP] | Japan | 6-095086 |
| May 25, 1994 | [JP] | Japan | 6-110833 |

[51] Int. Cl.[6] .................................................. H04B 7/216
[52] U.S. Cl. ........................ 370/342; 375/208; 455/33.2
[58] Field of Search ........................ 370/18, 342, 350, 370/441; 375/200, 205, 206, 207, 208, 209, 210; 455/33.2

[56] References Cited

U.S. PATENT DOCUMENTS

| 4,455,662 | 6/1984 | Gutleber | 375/207 |
| 4,672,658 | 6/1987 | Kavehrad et al. | 375/207 |
| 4,759,034 | 7/1988 | Nagazumi | 375/208 |
| 4,969,159 | 11/1990 | Belcher et al. | 375/207 |
| 5,022,047 | 6/1991 | Dixon et al. | 375/208 |
| 5,103,459 | 4/1992 | Gilhousen et al. | 375/205 |
| 5,179,571 | 1/1993 | Schilling | 375/205 |

FOREIGN PATENT DOCUMENTS 0 216974 | 4/1987 | European Pat. Off. .

*Primary Examiner*—Benedict V. Safourek
*Attorney, Agent, or Firm*—Oblon, Spivak, McClelland, Maier & Neustadt, P.C.

[57] ABSTRACT

CDMA mobile communication method and system for realizing an autonomous distributed control of radio channel allocation, a synchronization control for a smooth establishment/switching, and a VOX control for a capacity increase are provided. At either one station of each base station and the mobile station, one of a plurality of prescribed short spread codes is selected, and a data sequence to be transmitted is spread by using the selected short spread code and a prescribed long spread code and then transmitted, while at another one station, the data sequence before spreading is reproduced and received by despreading the data sequence from that either one station by using the selected short spread code and the prescribed long spread code. At a time of the handover, each one of data to be communicated between a handover source base station and the mobile station and data to be communicated between a handover target base station and the mobile station is spread by using both a long spread code and a short spread code, and the received data are composed by adjusting timings at each of the mobile station and the base station. Also, a VOX control is carried out for transmission frames to be transmitted through a radio channel in at least one of each base station and the mobile station, and transmitted by randomly allocating an offset with respect to a transmission timing for each channel from a plurality of prescribed offset amounts.

44 Claims, 24 Drawing Sheets

FIG.7

| | COMMON SPREAD CODE | IDENTIFICATION SPREAD CODE |
|---|---|---|
| BASE STATION $12_1$ | $C_{C1}=G(a)$<br>$C_{C2}=G(b)$<br>$\vdots$<br>$C_{Cm}=G(p)$ | $C_{I1}=G(I'_1)$ |
| BASE STATION $12_2$ | $C_{C1}=G(a)$<br>$C_{C2}=G(b)$<br>$\vdots$<br>$C_{Cm}=G(p)$ | $C_{I2}=G(I'_2)$ |
| $\vdots$ | $\vdots$ | $\vdots$ |
| BASE STATION $12_n$ | $C_{C1}=G(a)$<br>$C_{C2}=G(b)$<br>$\vdots$<br>$C_{Cm}=G(p)$ | $C_{In}=G(I'_n)$ |

FIG.10

| PERCH CH | SHORT CODE | LONG CODE |
|---|---|---|
| | G(128)  G(128, n) ...... G(128, 0) | NONE |

FIG.11

| | SHORT CODE | LONG CODE |
|---|---|---|
| CONTROL (UPWARD) COMMUNICATION (DOWNWARD) | G(128)  G(128, 128) — FOR COMMUNICATION  G(128, n1+1)  G(128, n1) — FOR CONTROL  ......  G(128, 0) | LONG CODE FOR EACH BASE STATION  · Uniquely determined from base station ID and perch code, no overlap  · Length : $2^{33}$ bit |

· A plurality of G(128) are allocated to one mobile station in multi-code communication
· G(128) that can tolerate interference is confirmed and then allocated

FIG.12

| | SHORT CODE | LONG CODE |
|---|---|---|
| CONTROL (UPWARD) | G(128) ...... G(128, n1) G(128, 0) } FOR CONTROL | LONG CODE FOR EACH BASE STATION<br>· Uniquely determined from base station ID and perch code, no overlap<br>· Length : $2^{33}$ bit |
| COMMUNICATION (UPWARD) | G(128) ...... G(128, 128) G(128, n1+1) } FOR COMMUNICATION  G(128, n1) G(128, 0) } FOR CONTROL | LONG CODE FOR EACH MOBILE STATION<br>· Uniquely determined from mobile station ID, no overlap<br>· Length : $23^{33}$ bit |
| | · A plurality of G(128) are allocated to one mobile station in multi-code communication<br>· G(128) that can tolerate interference is confirmed and them allocated<br>· All short codes may be used for communication without distinguishing those for control and those for communication | |

⟨CONSTITUENT ELEMENTS OF LONG CODE FOR DOWNWARD
CONTROL CHENNEL & DOWNWARD COMMUNICATION CHANNEL⟩

⟨CONSTITUENT ELEMENTS OF LONG CODE FOR
UPWARD CONTROL CHANNEL⟩

⟨CONSTITUENT ELEMENTS OF LONG CODE FOR
UPWARD COMMUNICATION CHANNEL⟩

FIG 22A  LONG CODE PHASE DATA(1)          10ms

PERCH CHANNEL

FIG 22B
CONTROL CHANNEL
(DOWNWARD/
TRANSMISSION)
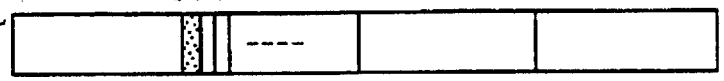

PROPAGATION   MOBILE STATION
FIG 22C  DELAY       RECEPTION TIMING

PERCH CHANNEL
(RECEPTION)

FIG 22D
CONTROL CHANNEL
(DOWNWARD/
RECEPTION)

MOBILE STATION
FIG 22E                    TRANSMISSION TIMING
CONTROL CHANNEL
(UPWARD/
TRANSMISSION)
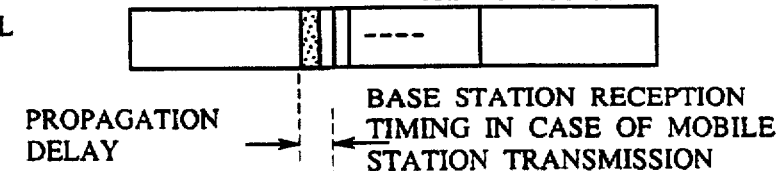

PROPAGATION    BASE STATION RECEPTION
DELAY          TIMING IN CASE OF MOBILE
               STATION TRANSMISSION

FIG 22F
CONTROL CHANNEL
(UPWARD/RECEPTION)

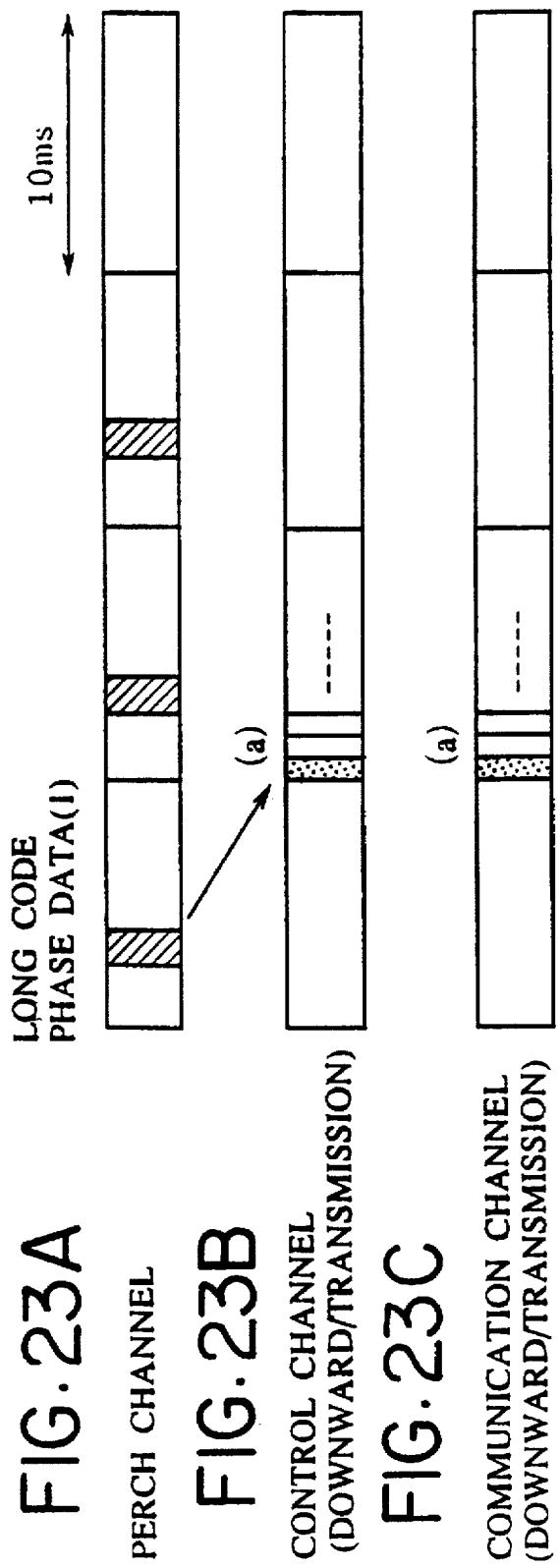

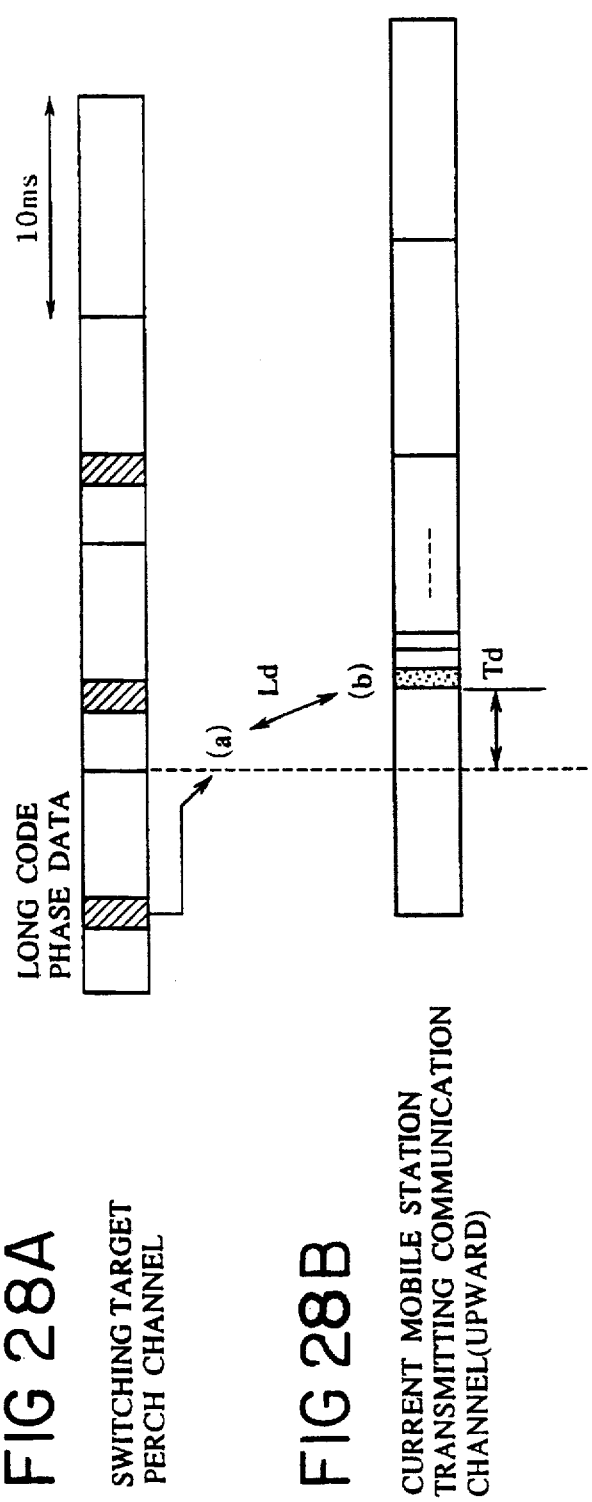
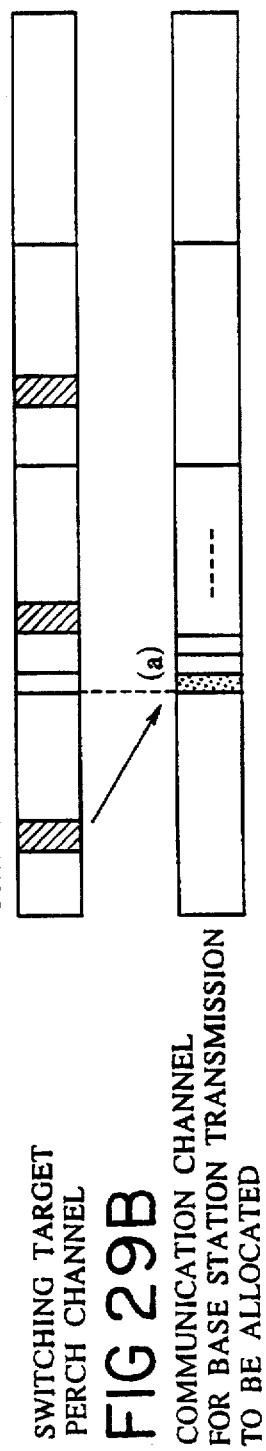
FIG 28A SWITCHING TARGET PERCH CHANNEL
FIG 28B CURRENT MOBILE STATION TRANSMITTING COMMUNICATION CHANNEL(UPWARD)
FIG 29A SWITCHING TARGET PERCH CHANNEL
FIG 29B COMMUNICATION CHANNEL FOR BASE STATION TRANSMISSION TO BE ALLOCATED

METHOD AND SYSTEM FOR CDMA MOBILE COMMUNICATION

TECHNICAL FIELD

The present invention relates to a method and a system for making a mobile communication in a CDMA (Code Division Multiple Access) scheme between mobile stations and base stations.

BACKGROUND ART

In a mobile communication, in order to utilize radio channels effectively, the identical radio channel is repeated utilized at base stations which are sufficiently distanced spatially. In such a case, in order to prevent a mutual interference of that identical radio channel, there are a fixed channel allocation scheme in which a radio propagation state within a service area is conjectured by an actual measurement, a theoretical calculation, etc., and a radio channel is fixedly provided at each base station, and a dynamic channel allocation scheme in which a radio channel that is available in a system as a whole is made available at any base station.

In the fixed channel allocation scheme, even when a radio channel which is allocated to a neighboring base station is available at an own base station, it is impossible to allocate that radio channel to a new radio channel allocation request within the own base station, so that a radio channel utilization efficiency is insufficient in that regard, and a considerable amount of efforts are required for a re-designing in a case of additionally providing a base station, etc., so that the adaptivity to a system expansion is low.

On the other hand, in the dynamic channel allocation scheme, it is possible to allocate the radio channel flexibly to some extent with respect to the temporal variation, the spatial bias, etc. of the traffic, and it is possible to suppress a call loss rate or an interference obstruction probability to be minimum.

However, in a conventional dynamic channel allocation scheme, a centralized control of allocations of the radio channels to the base stations at a control station is used, so that in order to suppress the call loss rate or the interference obstruction probability to be minimum, it requires an enormous amount of data and a complicated control, and there has been a drawback that the traffic of the signals between each base station and the control station increases.

Also, presently, as an automobile telephone or portable telephone system, a mobile communication system for making communications by a communication scheme such as a CDMA mobile communication scheme between mobile stations and base stations is considered.

Such a mobile communication system using the CDMA mobile communication scheme is equipped with base stations provided in cells constituting an area in which communications are possible, and mobile stations, and at a time of starting a communication between a mobile station and a base station or carrying out a channel switching, etc., after a frequency to be used in a communication and a spread code in the CDMA scheme are determined by using an upward control channel, a downward control channel, etc., between a mobile station and a base station, a communication is made by establishing a synchronization of an upward communication channel and a downward communication channel between a mobile station and a base station.

The base station is equipped with an antenna for making transmission and reception of radio link signals, a common amplifier circuit for amplifying the radio link signals to be transmitted or received through this antenna, a plurality of transceiver circuits for carrying out a radio link signal transmission and reception processing through this common amplifier circuit and a processing for communicating with an exchanger side through each wire link, and a base station control circuit for controlling transmission and reception operation of each of these transceiver circuits.

At a time of starting a communication with a mobile station or carrying out a channel switching, etc., after a frequency to be used in a communication and a spread code in the CDMA scheme are determined by using an upward control channel, a downward control channel, etc., between a mobile station and a base station, this base station makes a communication with said mobile station by establishing a synchronization of an upward communication channel and a downward communication channel between said mobile station and itself.

Also, the mobile station is equipped with an antenna for making transmission and reception of radio link signals, an amplifier circuit for amplifying the radio link signals to be transmitted or received through this antenna, a transceiver circuit for carrying out a radio link signal transmission and reception processing through this amplifier circuit, an input/output circuit having a microphone, a loudspeaker, etc., for carrying out input/output of speeches, an operation circuit having man-machine interfaces such as a dial buttons, a display, etc., and a mobile station control circuit for controlling said transmission and reception circuit according to operation contents of this operation circuit.

At a time of starting a communication with a base station or carrying out a channel switching, etc., after the data indicating the frequency and the spread code transmitted from said base station by using the upward control channel, the downward control channel, etc., is received and this is stored, this mobile station makes a communication with said base station by establishing a synchronization between said base station and itself for the upward communication channel and the downward communication channel.

In this case, as a procedure for switching the communication channel, the procedure described in the following is used.

First, while a communication is made by using one channel between the mobile station and the base station, when the communication quality of this channel is degraded, as shown in FIG. 1, this is detected by the transceiver circuit in communication at the base station side, and a quality degradation notice is issued to the base station control circuit. Then, by the base station control circuit which received this, one channel which is idle is selected among a plurality of channels provided, and after the spread code corresponding to this channel is determined to be a switching target spread code, the control data designating the switching target spread code is transmitted to the mobile station side through the control channel associated with the communication channel currently in communication.

Then, after the control data designating the switching target spread code is received by the mobile station control circuit of the mobile station, a confirmation data indicating that this has been confirmed is generated, and when this is transmitted to the base station control circuit at the base station side through the control channel associated with the communication channel currently in communication, the switching target spread code is supplied to the transceiver circuit currently in communication with the mobile station by this base station control circuit, and whether the confirmation signal indicating that this has been held is outputted from the transceiver circuit or not is checked.

After that, a change of the synchronization data indicating that it has become possible to switch to the switching target spread code is carried out at the mobile station side, and this is confirmed by the transceiver circuit at the base station side, while a change of the synchronization data indicating that it has become possible to switch to the switching target spread code is carried out at the transceiver circuit of the base station side, and when this is confirmed by the transceiver circuit of the mobile station, the communication channel is changed at the transceiver circuit of the mobile station side as the switching of the spread code is carried out at a prescribed timing that is set up in advance, while the communication channel is changed at the transceiver circuit of the base station side as the switching of the spread code is carried out, and the communication between the mobile station and the base station in the switching target communication channel is started.

However, in the mobile communication system using such a conventional CDMA mobile communication scheme, because it is necessary to use mutually different codes which have small correlation with each other as the spread codes to be provided at respective communication channels, it is necessary to use long spread codes when a number of communication channels is increased, and there has been a problem that an excessive time is taken until a phase of the spread code obtained by a code generation circuit in a sliding correlator or a matched filter circuit provided in each transceiver circuit is made to coincide with a phase of the spread code which is modulating the received signals.

For this reason, there has been a problem that an excessive time is taken until the communication channel is established.

Next, as shown in FIG. 2, when a plurality of base stations such as a first base station and a second base station are existing, a procedure for a time at which the handover is activated as the mobile station moves in cells covering the first and second base stations will be explained. Here, in this FIG. 2, it is assumed that the mobile station moves from a cell of the first base station to a cell of the second base station.

First, while a communication is made by using one communication channel between the mobile station and the first base station, when it is judged that the mobile station has moved to the second base station as a result of the moving of the base station, this is detected (cell transition detection) by the transceiver circuit of the mobile station, and notified to the mobile station control circuit.

Then, by this mobile station control circuit, a handover request is made with respect to the base station control circuit of the first base station through the control channel associated with the communication channel, and the handover processing of the base station control circuit in this first base station is activated.

By means of this, a link set up request is transmitted to the base station control circuit of the second base station by the base station control circuit of the first base station, and a set up of the wire link is made by the base station control circuit of the second base station which received this, while the spread code of a new channel is selected, one of the transceiver circuits of the second base station is activated by the selected spread code, and the transmission/reception by the designated spread code is started by this transceiver circuit.

Next, by the base station control circuit of the second base station, when the activation and start of the transmission/ reception using the spread code of the new channel by said transceiver circuit is confirmed, a link set up completion is notified to the base station control circuit of the first base station, while a channel designation request for making the selected spread code designated to the mobile station is transmitted.

Then, the designated spread code is notified to the mobile station by the base station control circuit of the first base station which received this, while the channel designated content is analyzed by the mobile station control circuit of this mobile station, and the spread code obtained by this analysis processing is set up to the transceiver circuit.

By means of this, the spread code is switched to the designated one by the transceiver circuit of the mobile station, and the communication channel with the second base station is established. Here, however, in such a mobile communication system using the CDMA mobile communication scheme, in a case of carrying out the soft handover for making simultaneous connections with a plurality of base stations, a plurality of correlators are provided in the transceiver circuit, and by each of these correlators, a new communication link with the second base station is established while maintaining the communication with the first base station.

However, in such a mobile communication system using a conventional CDMA mobile communication scheme, in addition to the above described problem that it takes too much time for a synchronization for the purpose of the communication channel establishment, there has been a problem that the synchronized capturing is nearly impossible in a case the handover source base station and the handover target base station are out of synchronization.

For this reason, there has been such problems that the communication is disconnected as the handover target base station fails to make a synchronization capturing at a time of the handover, or even if it succeeds to make a synchronization capturing, it takes too much time until the synchronization establishment, so that the smooth handover cannot be made, etc.

Also, conventionally, in order to reduce a transmission power of a transmitter and an interference given to the other, there is a control called VOX (Voice Operation Transmitting) in which a transmission is made only at times in which there are data to be transmitted, and a transmission is not made at other times. Here, the VOX is usually a control for turning a transmission ON/OFF according to presence/absence of speeches, but in the present application, it is treated in a wider sense as that which includes a transmission ON/OFF control according to presence/ absence of not just speeches but also data to be transmitted.

In the VOX control, it is basic not to make a transmission at times in which there is no data to be transmitted, but in an actual implementation, it is not possible not to transmit an entire frame without data. For example, in an exemplary radio frame configuration shown in FIG. 3, PR is a preamble for a clock reproduction at a time of reception, SW is a synchronization word for a frame synchronization, INFO is data to be transmitted. Here, when it is attempted to make a synchronization from a state which is totally out of synchronization, several tens bits are necessary for the preamble, and assuming that one frame is at most 200 to 300 bits, it is inefficient to provide several tens bits of the preamble which carries no data in each frame, and also, if it is in a state in which a synchronization has already been made to some extent, it suffices for the preamble to have 1 to 2 bits as it only confirms or maintains the clock synchronization, so that the usual frame after the channel establishment is made to have the preamble in a less number of bits. However, in such a configuration, if a control for not transmitting an entire frame when there is no data to be transmitted is carried out, it becomes impossible to make a communication as it becomes out of synchronization. For this reason, conventionally, in order to maintain the synchronization, a method for not transmitting data portion alone and transmitting the other portion has been adopted.

On the other hand, in the CDMA mobile communication scheme, a communication is made by separating and multiplexing a plurality of channels by the spread codes in one frequency, so that if there is a transmitter which is transmitting in overlap with the own transmission signals, it is going to be the interference. Whether it can be received by a receiver depends on a ratio of the own station signals and the interference, and a possibility for successful reception becomes greater when the ratio is larger, i.e., when the interference is smaller. Also, with the configuration in which the interference is as small as possible, it is possible to make a number of simultaneous communication channels large, and therefore it is possible to make a system with a large subscriber capacity.

Here, while a plurality of radio channels are established as shown in FIG. 4, when the VOX control is carried out, the radio channels are mutually synchronized within one base station, so that the average transmission power can be made smaller by the VOX control, but the synchronization word portions overlap with each other and the reception quality for the synchronization word portions will be lowered. In other words, even when the interference given to the other is made smaller by turning the transmission OFF for the data portion on purpose, the capacity is determined by the synchronization word section, and there has been a drawback that the capacity increase cannot be achieved even when the VOX is used.

DISCLOSURE OF THE INVENTION

The object of the present invention is to provide CDMA mobile communication method and system in which no control station is required in a dynamic channel allocation scheme, a radio channel is autonomously allocated by an own base station alone, and in addition, a call loss rate and an interference obstruction probability are small.

Also, another object of the present invention is to provide CDMA mobile communication method and system capable of making a phase of the spread code obtained at a code generation circuit coinciding with a phase of the spread code modulating the received signals in short time, even when each spread code becomes long, and by means of this, carrying out the establishment and the switching of the communication channels smoothly while drastically increasing a number of communication channels between the mobile stations and the base stations.

Also, another object of the present invention is to provide CDMA mobile communication method and system capable of making a phase of the spread code obtained at a code generation circuit coinciding with a phase of the spread code modulating the received signals in short time, even when each spread code becomes long, and by means of this, carrying out the switching of the communication channels at a time of the handover smoothly while drastically increasing a number of communication channels between the mobile stations and the base stations.

Also, another object of the present invention is to provide CDMA mobile communication method and system capable of constructing a system with a large capacity by utilizing a reduction of an amount of interference in a case of carrying out the VOX control for a system capacity increase.

According to one aspect of the present invention, there is provided a CDMA mobile communication method in a CDMA mobile communication system formed by a plurality of base stations and at least one mobile station which communicate in a CDMA scheme through radio channels, comprising: a step of selecting one of a plurality of prescribed short spread codes, and transmitting by spreading data sequence to be transmitted by using the selected short spread code and a prescribed long spread code with a code length longer than said short spread code, at either one station of each base station and the mobile station; and a step of receiving the data sequence from said either one station, and reproducing the data sequence before spreading by despreading the received data sequence by using said selected short spread code and said prescribed long spread code, at another one station of each base station and the mobile station.

Also, according to another aspect of the present invention, there is provided a CDMA mobile communication method in a CDMA mobile communication system formed by a plurality of base stations and at least one mobile station which communicate in a CDMA scheme through radio channels, comprising: a step of communicating by spreading each one of data to be communicated between a handover source base station and the mobile station and data to be communicated between a handover target base station and said mobile station by using both a long spread code and a short spread code; a step of carrying out a handover by composing data received from the handover source base station and data received from the handover target base station by adjusting timings at said mobile station; and a step of carrying out a handover by composing data received from the mobile station at a cell of handover source and data received from the mobile station at a cell of handover target by adjusting timings at each base station or an upper level device connected to that base station.

Also, according to another aspect of the present invention, there is provided a CDMA mobile communication method in a CDMA mobile communication system formed by a plurality of base stations and at least one mobile station which communicate in a CDMA scheme through radio channels, comprising: a step of controlling transmission frames to be transmitted through at least one radio channel such that a transmission of a data portion is not carried out for a frame without data to be transmitted, in at least one of each base station and the mobile station; a step of randomly allocating an offset with respect to a transmission timing for each channel from a plurality of prescribed offset amounts; and a step of transmitting said transmission frames through each channel at a transmission timing with the offset allocated by said step of allocating.

Also, according to another aspect of the present invention, there is provided a CDMA mobile communication system formed by a plurality of base stations and at least one mobile station which communicate in a CDMA scheme through radio channels, in which: either one station of each base station and the mobile station has means for selecting one of a plurality of prescribed short spread codes, and means for transmitting by spreading data sequence to be transmitted by using the selected short spread code and a prescribed long spread code with a code length longer than said short spread code; and another one station of each base station and the mobile station has means for receiving by reproducing the data sequence before spreading by despreading the data sequence from said either one station by using said selected short spread code and said prescribed long spread code.

Also, according to another aspect of the present invention, there is provided a CDMA mobile communication system formed by a plurality of base stations and at least one mobile station which communicate in a CDMA scheme through radio channels, in which: each base station and the mobile station have means for communicating by spreading each one of data to be communicated between a handover source base station and the mobile station and data to be communicated between a handover target base station and said mobile station by using both a long spread code and a short spread code; said mobile station further has means for carrying out a handover by composing data received from the handover source base station and data received from the handover target base station by adjusting timings; and said each base station or an upper level device connected to that base station further has means for carrying out a handover by composing data received from the mobile station at a cell of handover source and data received from the mobile station at a cell of handover target by adjusting timings.

Also, according to another aspect of the present invention, there is provided a CDMA mobile communication system formed by a plurality of base stations and at least one mobile station which communicate in a CDMA scheme through radio channels, having: means for controlling transmission frames to be transmitted through at least one radio channel such that a transmission of a data portion is not carried out for a frame without data to be transmitted, in at least one of each base station and the mobile station; and means for transmitting by randomly allocating an offset with respect to a transmission timing for each channel from a plurality of prescribed offset amounts.

BRIEF DESCRIPTION OF THE DRAWINGS

FIG. 7 is a figure showing a table summarizing common spread codes and identification spread codes used in the CDMA mobile communication system of FIG. 6.

FIG. 10 is a figure showing an exemplary spread code configuration for a perch channel used in the CDMA mobile communication system according to the second and third embodiments of the present invention.

FIG. 11 is a figure showing an exemplary spread code configuration for a downward control channel and a downward communication channel used in the CDMA mobile communication system according to the second and third embodiments of the present invention.

FIG. 12 is a figure showing an exemplary spread code configuration for an upward control channel and an upward communication channel used in the CDMA mobile communication system according to the second and third embodiments of the present invention.

FIG. 22 is a timing chart showing exemplary timings since a reception of a perch channel until a transmission of an upward control channel at a mobile station in the CDMA mobile communication system of FIG. 17.

FIG. 23 is a timing chart showing an exemplary timing for a long code at a time of a downward communication channel generation at a base station in the CDMA mobile communication system of FIG. 17.

FIG. 28 is a timing chart showing exemplary timings for a perch channel frame received and an upward communication channel frame transmitted at a mobile station in the CDMA mobile communication system of FIGS. 24 and 25.

FIG. 29 is a timing chart showing exemplary timings for a perch channel frame and a downward communication channel frame transmitted at a handover target base station in the CDMA mobile communication system of FIGS. 24 and 25.

BEST MODE FOR CARRYING OUT THE INVENTION

Figure 1:
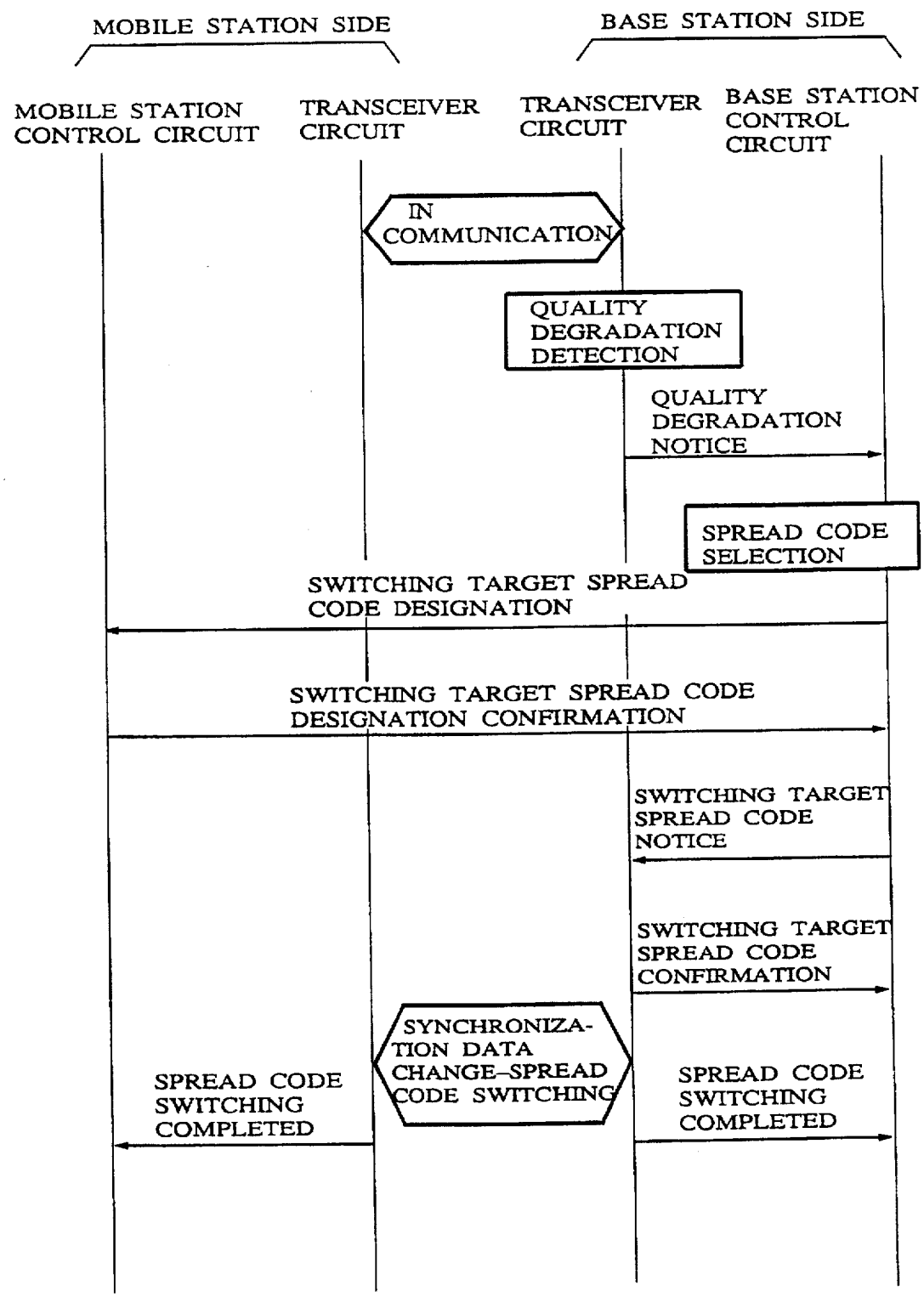
FIG. 1 is a sequence chart showing a channel switching procedure by a conventional CDMA mobile communication method.
Figure 2:
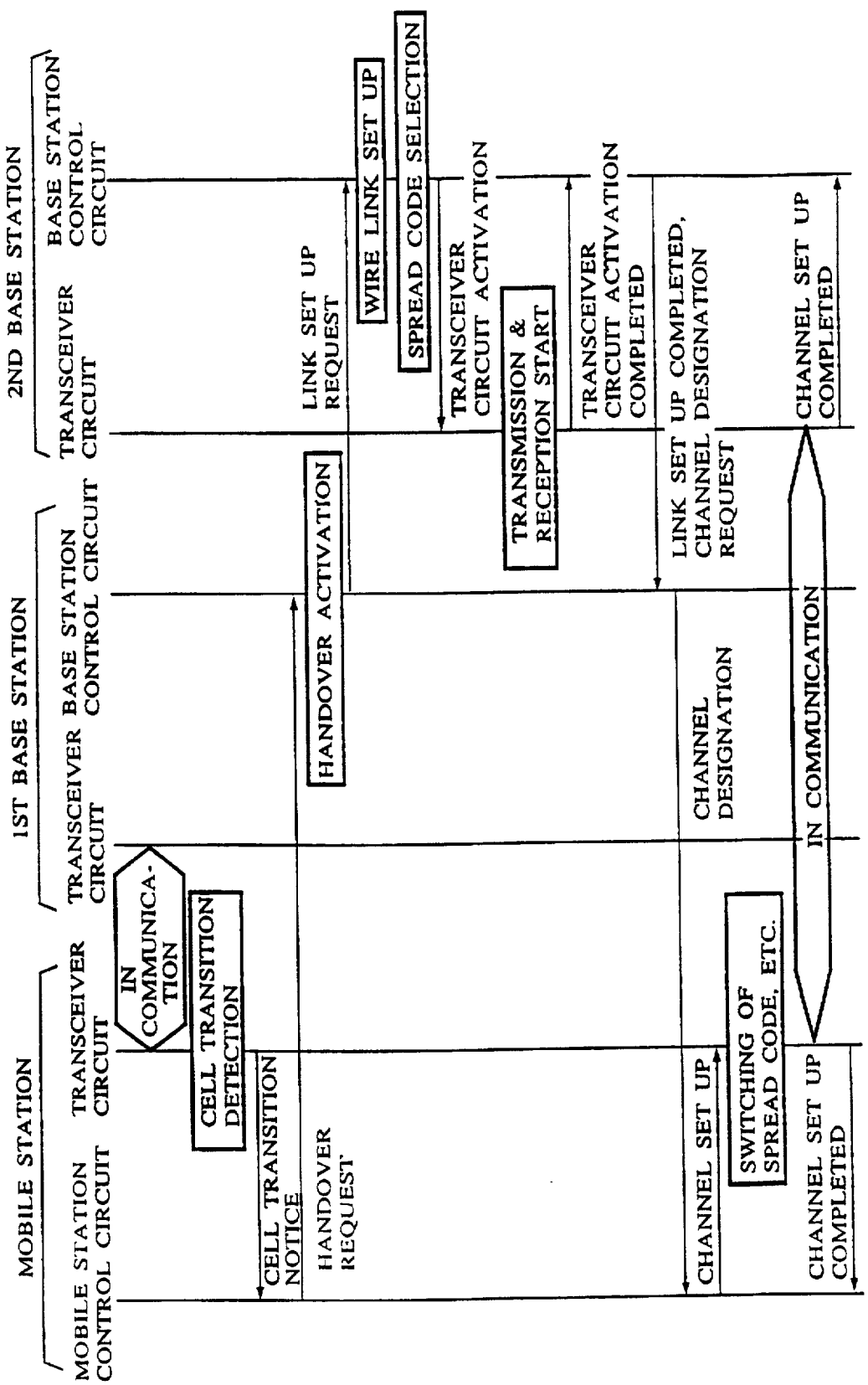
FIG. 2 is a sequence chart showing a channel switching procedure at a time of the handover by a conventional CDMA mobile communication method.
Figure 3:
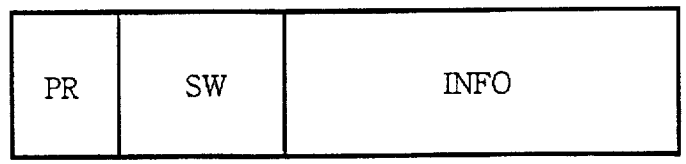
FIG. 3 is a diagram showing an exemplary configuration of a radio channel in a conventional mobile communication method.
Figure 4:
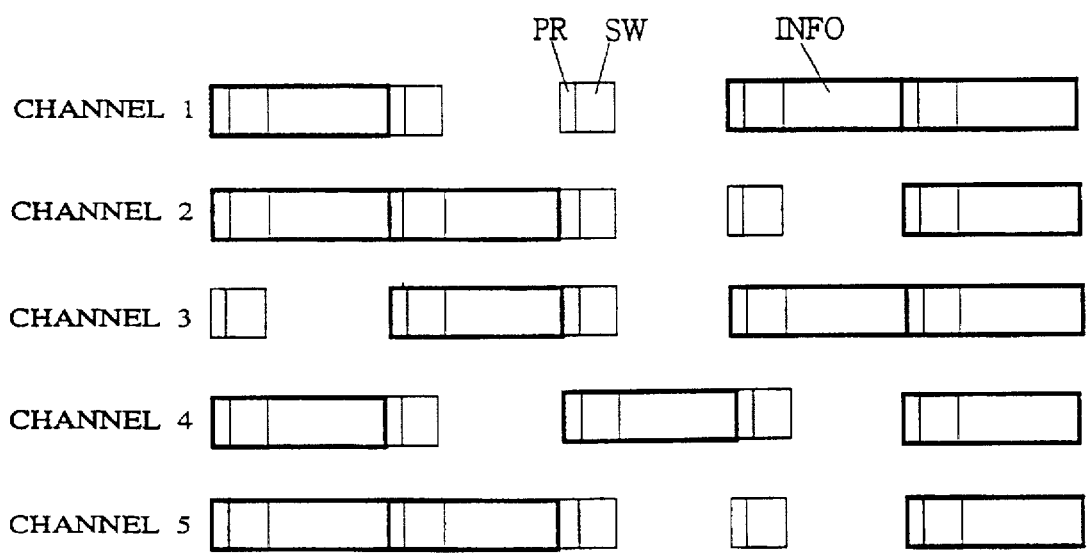
FIG. 4 us a timing chart showing a frame transmission state at a time of the VOX control of a plurality of channels in a conventional mobile communication scheme.
Figure 5:
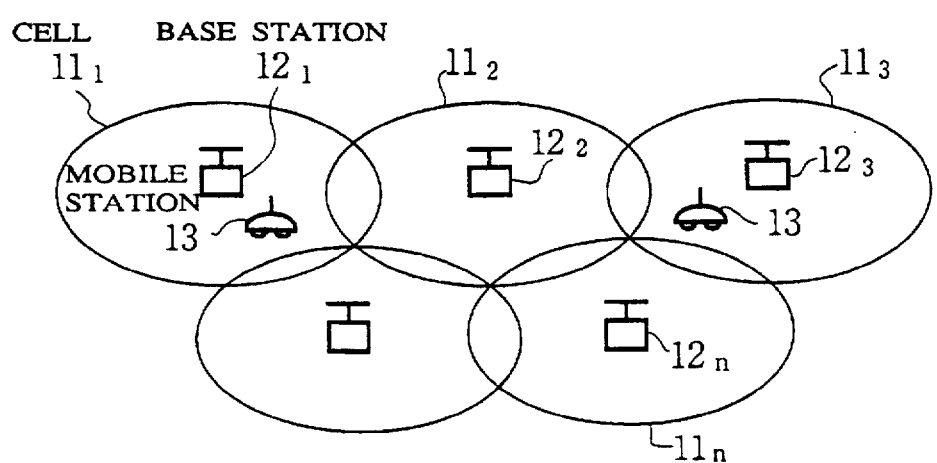
FIG. 5 is a schematic diagram showing an overall configuration of a CDMA mobile communication system according to the first embodiment of the present invention.

FIG. 5 is that which shows an overall configuration of a CDMA mobile communication system according to the first embodiment of the present invention, where a service area is divided into a plurality of cells (zones) $11_1$ to $11_n$, base stations $12_1$ to $12_n$ are provided in respective cells $11_1$ to $11_n$, and a communication is made between each mobile station 13 moving in these cells and each base station 12.

Figure 6:
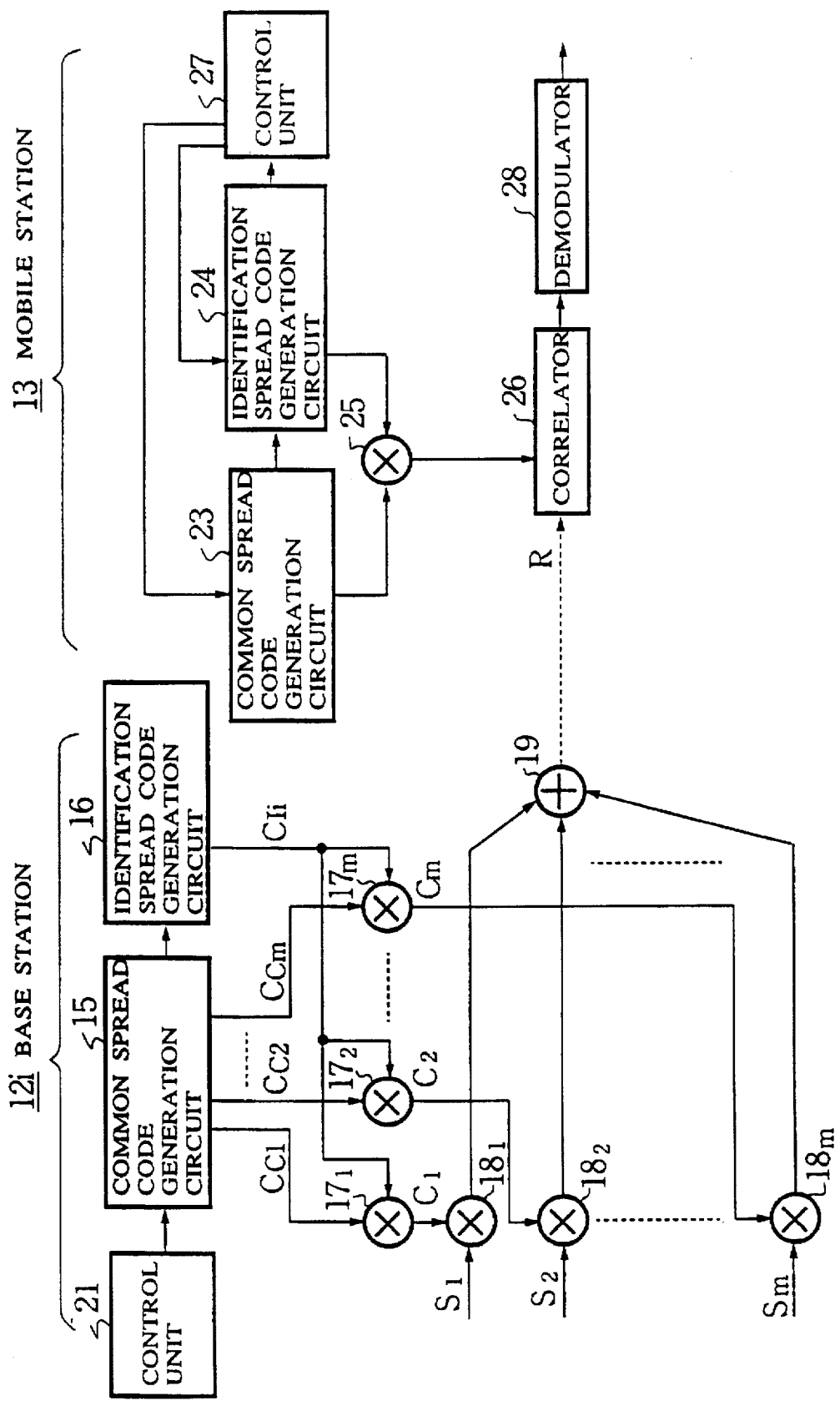
FIG. 6 is a block diagram showing a configuration of a main portion of a base station and a mobile station in a CDMA mobile communication system according to the first embodiment of the present invention.

Each base station $12_i$ (i=1, 2, . . . . . . . . , n) and each mobile station 13 have a configuration as shown in FIG. 6. Here, in FIG. 6, only those portions related to the essence of the present invention are shown.

Each base station $12_i$ has a common spread code generation circuit 15 and an identification spread code generation circuit 16, and the common spread code generation circuit 15 is capable of selectively generating one or more of a plurality of common spread codes $C_{C\ 1}$ to $C_{C\ m}$ which are common to the base stations $12_1$ to $12_n$, with respect to one or more of the mobile station 13, and the identification spread code generation circuit 16 generates an identification spread code $C_{I\ i}$ unique to that base station $12_i$.

In the following, an exemplary case of generating each of the common spread codes $C_{C\ j}$ (j=1, 2, . . . . . . . . , m) and the identification spread code $C_{I\ i}$ as Gold sequences will be explained. Here, the Gold sequence is generated by giving different bit patterns to two shift registers for m sequence generation as an initial state, and when the bit pattern in the initial state of one of these shift registers is denoted as x, for the initial state of the other shift register, a pattern which does not coincide with the pattern x and which is not entirely "0" is set up as the initial state. Here, the Gold sequence generated by the setting pattern x in the initial state as described above will be denoted by G(x).

For example, as shown in FIG. 7, it is made such that each base station $12_i$ can generate a plurality of identical common spread codes $C_{C\ 1}$=G(a) to $C_{C\ m}$=G(p). Also, each base station $12_i$ generates the unique identification spread code $C_I$ =G($\Gamma_i$). As the identification spread code $C_{I\ i}$, a pattern $\Gamma_i$ in which the identifier of the base station $12_i$ (such as a base station number) for example and a predetermined bits are combined is used for the initial state.

As a concrete example, a bit pattern in which the first bit to the twenty-sixth bit from top are given by the base station identifier $I_i$, and the next 14 bits from twenty-seventh bit to the fortieth bit are given by prescribed bits is used. Here, without using the identifier $I_i$ directly, it may be possible to use the bit pattern in which the identifier $I_i$ is converted according to predetermined rules. Also, $I_i$ may be used directly as $\Gamma_i$ without combining any other bits with $I_i$. In essence, by using that which contains what is corresponding to the identifier $I_i$ of each base station $12_i$ as the initial state bit pattern for the identification spread code in each base station $12_i$, a unique spread code is obtained at each base station $12_i$.

A total number of the identification spread codes $C_{I\ i}$ is set to be greater than or equal to a total number of cells or mobile stations utilized in that CDMA mobile communication system. Also, a number m of the common spread codes $C_{C\ 1}$ to $C_{C\ m}$ is set to be greater than or equal to a total number of radio channels necessary at a cell supported by each base station. In other words, a number of bits N in the initial state pattern of the common spread code is set such that its number of codes $2^N+1$ becomes greater than m, and at the same time it becomes a sufficient number for obtaining a required spread gain from a viewpoint of the demodulation of one symbol. A number of bits M in the initial state pattern of the identification spread code $C_{I\ i}$ is set such that its number of codes $2^M+1$ becomes greater than or equal to a number n of base stations. Also, in a case of utilizing an identifier $I_i$ of each base station $12_i$ for the initial state of the identification spread code $C_{I\ i}$ as described above, this number of bits M becomes greater than or equal to a number of bits in the identifier of each base station $12_i$. By means of this, in a case a number of bits in the initial state pattern of the identification spread code $C_{I\ i}$ is 26, a number of codes becomes $2^{26}+1$, and when there are as many as these, even when a number of base stations 12 is large, it is usually possible to give a unique one to each base station $12_i$. Also, in the present invention, a code length of the identification spread code usually becomes longer than the common spread code as in the above.

Returning to the explanation of FIG. 6, as in the above, at each base station $12_i$, m pieces of the common spread codes $C_{C\ 1}$ to $C_{C\ m}$ are generated, and also one identification spread code $C_{I\ i}$ is generated. Then, each of the common spread codes $C_{C\ 1}$ to $C_{C\ m}$ is selectively multiplied with the identification spread code $C_{I\ i}$. In FIG. 6, for a plurality of mobile stations 13, the common spread codes $C_{C\ 1}$ to $C_{C\ m}$ and the identification spread code $C_{I\ i}$ are respectively multiplied at multipliers $17_1$ to $17_m$, and the spread codes $C_1$ to $C_m$ which are their multiplication results are respectively multiplied with the input data sequences $S_1$ to $S_m$, for a plurality of mobile stations 13 at multipliers (spreaders) $18_1$ to $18_m$, such that each of the data sequences $S_1$ to $S_m$ is directly spread. These spread data sequences are composed at an adder 19 and transmitted to the base stations 13.

Actually, when one of the data sequences $S_1$ to $S_m$ is entered, one of the common spread codes $C_{C\ 1}$ to $C_{C\ m}$ which is not in use is selected, and this and the identification spread code $C_{I\ i}$ is multiplied, such that the input data sequence is going to be spread by that multiplication output sequence, and the control at this time is carried out by the control unit 21 of each base station $12_i$. Here, the common spread code generation circuit 15 and the identification spread code generation circuit 16 are mutually set in chip synchronization. Also, the output of the adder 19 is changed into radio frequency signals and irradiated as radio waves by a radio transmitter (not shown).

On the other hand, as shown in FIG. 6, the mobile station 13 has a common spread code generation circuit 23 and an identification spread code generation circuit 24, where it is possible to selectively generate one of the common spread codes $C_{C\ 1}$ to $C_{C\ m}$ from the common spread code generation circuit 23, and it is possible to selectively generate one of the identification spread codes $C_{I\,i}$ to $C_{I\,n}$ from the identification spread code generation circuit 24. Here, similarly as in a usual procedure, the radio channel to be used in a communication between the mobile station 13 and the base station $12_i$, i.e., one of the spread codes $C_1$ to $C_m$, in this case, is notified from the base station $12_i$ to the mobile station 13 through the control channel. Therefore, according to that notified spread code $C_j$, the mobile station 13 selectively generates the common spread code $C_{C\,j}$ and the identification spread code $C_{I\,i}$ according to that base station $12_i$, multiplies them at a multiplier 25, and reproduces the data sequence by despreading that multiplication output sequence with respect to the received spread sequence R at a correlator 26, and demodulating it at a demodulator 28. Here, the received spread sequence R is that which is converted into the baseband signals by a receiver (not shown). The control of the common spread code generation circuit 23 and the identification spread code generation circuit 24 is carried out by the control unit 27, and these generation circuits 23 and 24 are mutually set in chip synchronization.

In the above, the spread codes $C_i$ to $C_m$ generated by each base station $12_i$ become mutually different ones as the identification spread code $C_{I\,i}$ unique to that base station $12_i$ is used, and therefore without considering the radio channels (spread codes) in use at the other base stations, it is possible to determine the radio channel (spread code) in use by this base station $12_i$ itself alone.

Consequently, according to this first embodiment, it is made such that the data sequence is spread, or the received sequence is despread by the common spread code common to these base stations and the identification spread code unique to the base station simultaneously, such that the selection of the radio channel to be used at the base station can be made in a completely closed manner at the base station, and the so called autonomous distributed control is possible, while the control lines among the base stations can also be saved, so that it is possible to realize a method and a system for a CDMA mobile communication in which no control station is required in the dynamic channel allocation scheme, and the radio channel is allocated autonomously by the base station itself alone, and in addition, while the call loss rate and the interference obstruction probability are small.

Figure 8:
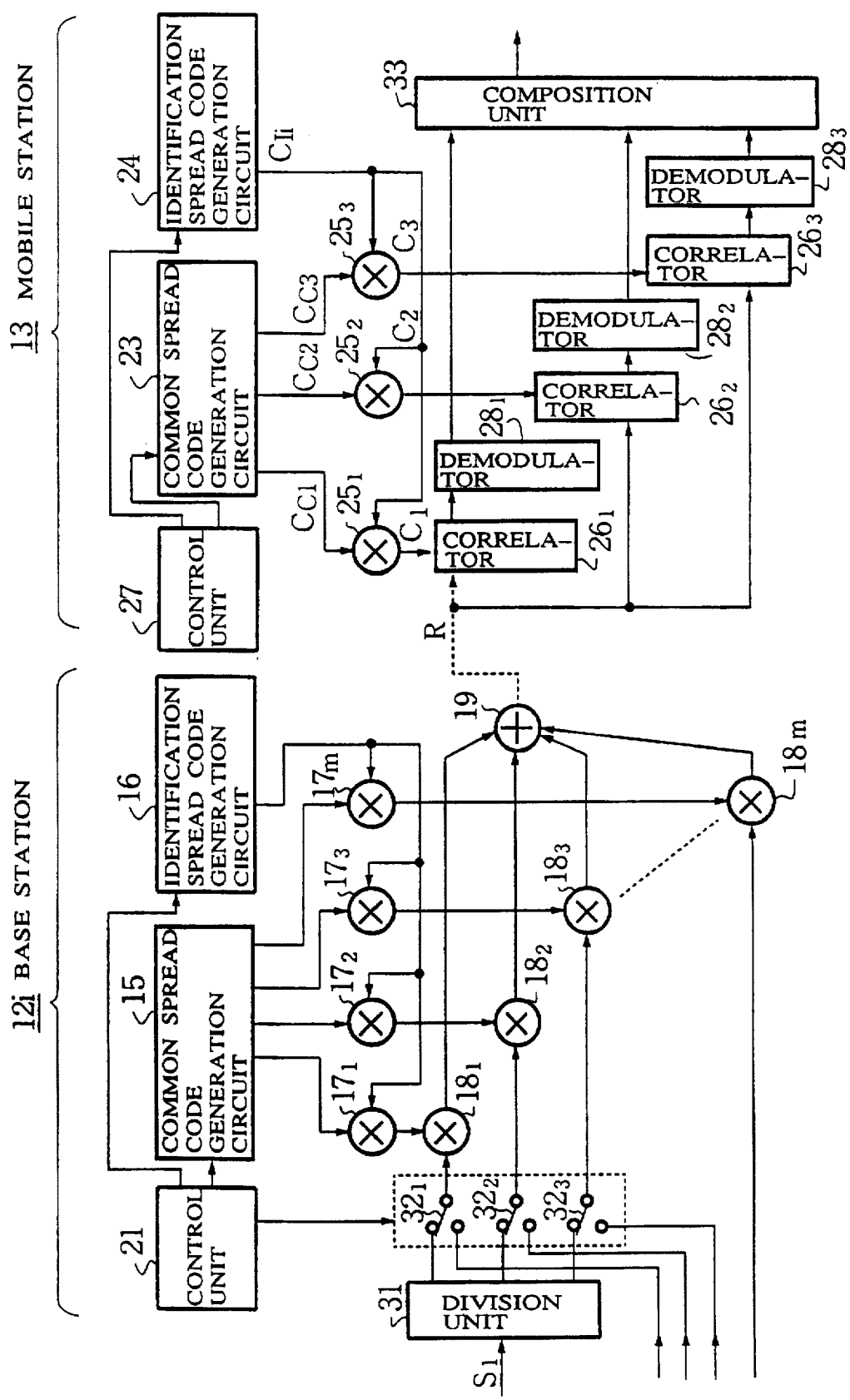
FIG. 8 is a block diagram showing one modification for the configuration of a main portion of a base station and a mobile station of FIG. 6.

Here, as a modification of the above described first embodiment, it is also possible to divide data which is greater than or equal to a transmission rate capable of being transmitted by one channel into r pieces, and transmit it by utilizing r channels. In that case, as shown in FIG. 8 by giving identical reference numerals to portions corresponding to FIG. 6, the data sequence $S_1$ is divided into three data sequences in ⅓ rate at a division unit 31 of each base station $12_i$ for example, and they are supplied to the multipliers $18_1$, $18_2$, and $18_3$ through switching switches $32_1$, $32_2$, and $32_3$, respectively, spread by the spread codes $C_1$, $C_2$, and $C_3$, respectively, and transmitted.

At the mobile station, the common spread codes $C_{C\,1}$, $C_{C\,2}$, and $C_{C\,3}$ are generated from the common spread code generation circuit 23 according to the notified spread codes $C_1$ to $C_3$, and also the identification spread code $C_{I\,i}$ is generated from the identification spread code generation circuit 24. Then, these are multiplied together at the multipliers $25_1$, $25_2$, and $25_3$ to produce the spread codes $C_1$, $C_2$, and $C_3$, and the received sequence R is despread by using them at the correlators $26_1$, $26_2$, and $26_3$, respectively, and demodulated at the demodulators $28_1$, $28_2$, and $28_3$. Then, their outputs are composed into a sequence in three times faster rate at the composition unit 33 of the mobile station 13, to obtain the original high speed data sequence.

Even in a case of making a high rate data transmission using a plurality of channels in this manner, by setting the identification spread code to be identical, it becomes possible to use a less number of stages for the shift registers in the code generation circuit, compared with a case of using a plurality of spread codes which are completely different from each other.

Also, as the correlator for carrying out the despreading in the above described first embodiment, the matched filter, the sliding correlator, etc. can be used. In addition, as the common spread codes and the identification spread code, not just the Gold sequences, but also the n sequences, the PN symbols, etc. may be used.

In addition, in the above described first embodiment, the the spread code $C_j$ is produced by multiplying the common spread code $C_{C\,j}$ and the identification spread code $C_{I\,i}$, and the data sequence is spread or the received sequence is despread by this spread code $C_j$, but it is also possible to spread the data sequence by the common spread code $C_{C\,j}$ or the identification spread code $C_{I\,i}$, and then spread that spread data sequence by the identification spread code $C_{I\,i}$ or the common spread code $C_{C\,j}$. In essence, it suffices to spread the data sequence simultaneously by the spread codes $C_{C\,j}$ and $C_{I\,i}$.

Similarly, it is possible to despread the received sequence by the common spread code $C_{C\,j}$ or the identification spread code $C_{I\,i}$, and then despread that despread sequence by the identification spread code $C_{I\,i}$ or the common spread code $C_{c\,j}$. In essence, it suffices to despread the received sequence simultaneously by the spread codes $C_{C\,j}$ and $C_{I\,i}$.

Next, an exemplary application of the above described first embodiment will be explained.

In FIG. 5, when the mobile station 13 moved from the cell $11_1$ to the cell $11_2$ while communicating with the base station $12_1$ for example, there is a need to switch to a communication with the base station $12_2$, and this switching is called the handover. At a time of this handover, a communication with an instantaneous disconnection can be carried out as the mobile station 13 simultaneously communicates with both of the handover source base station $12_1$, and the handover target base station $12_2$. To this end, conventionally, the identical spread code is used for the downward channels from the base stations $12_1$ and $12_2$, but in that case, in order for the symbols of the data from the both base stations $12_1$, and $12_2$ to reach to the mobile station 13 simultaneously, timings of the transmission data to the both base stations $12_1$ and $12_2$ are adjusted at an exchange station which is at an upper level of the base stations $12_1$ and $12_2$. However, there are cases in which the network transmission delay between the exchange station and the base stations $12_1$ and $12_2$ changes, and also the transmission delay in the radio section also changes depending on the transmission environment and the distance between the mobile station and the base station, so that it is difficult to maintain it such that the data symbols from a plurality of base stations always arrive simultaneously during the handover, and when the symbols are displaced, they are going to be the interferences with each other in the radio section, so that it has often been impossible to make a satisfactory communication without an instantaneous disconnection.

For this reason, by applying the above described first embodiment, it becomes possible to realize the satisfactory communication without an instantaneous disconnection easily, by making a communication between the handover source base station and the mobile station, and a communication between the handover target base station and this mobile station by using mutually different spread codes, and composing the data from the both base stations at adjusted timings in this mobile station.

For example, in FIG. 5, the base stations $12_1$ and $12_2$ are made to spread and transmit the identical data sequence from the identical exchange station by using the mutually different spread codes $C_1$ and $C_2$, respectively.

Figure 9:
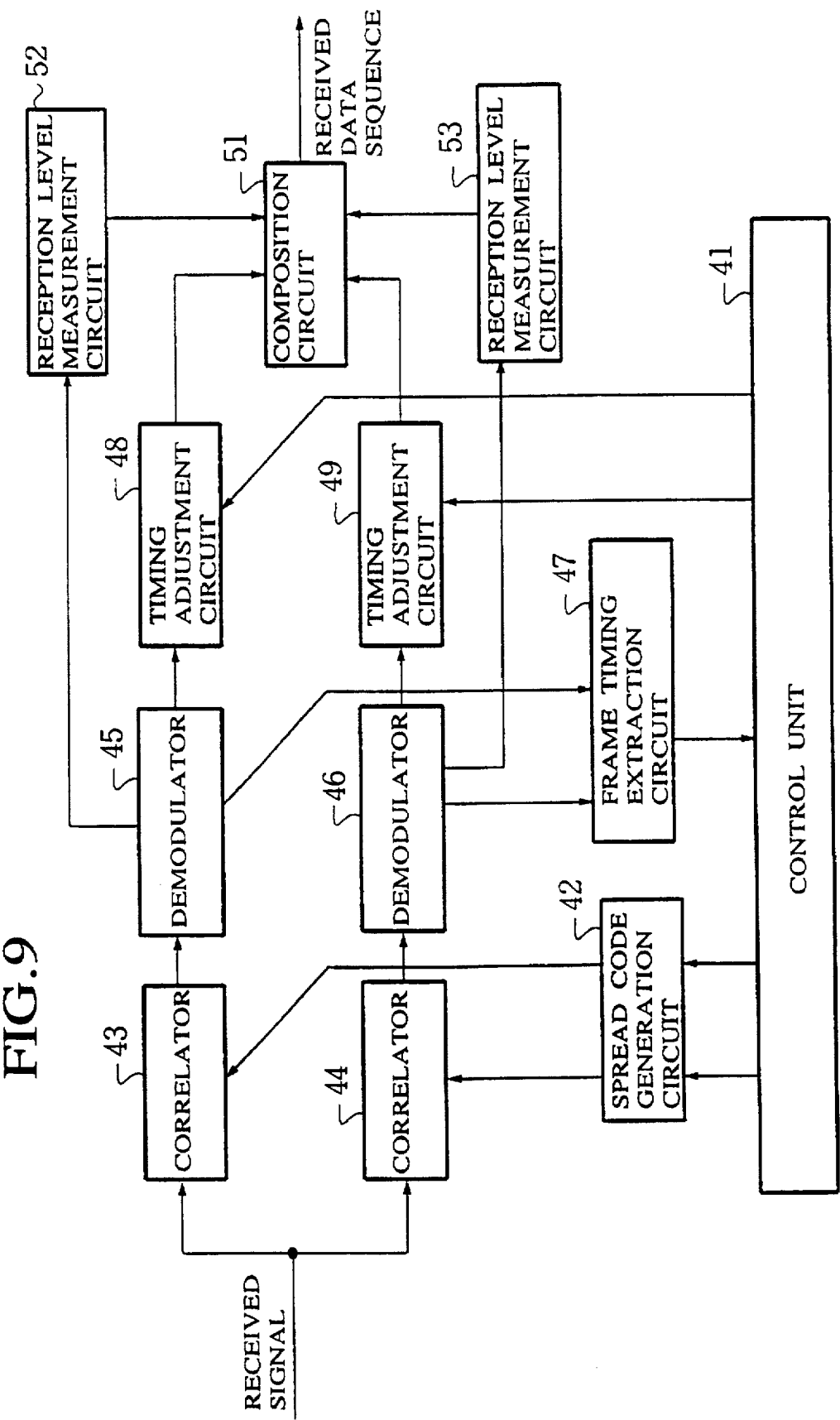
FIG. 9 is a block diagram showing a configuration of a mobile station in one application of the CDMA mobile communication system according to the first embodiment of the present invention.

On the other hand, the mobile station 13 is made to have a configuration as shown in FIG. 9 for example. Namely, when it is notified from the base station $12_1$ that the spread codes $C_1$ and $C_2$ are the channels that can be used during the handover, the control unit 41 sets them in the spread code generation circuit 42, and the spread code generation circuit 42 generates the spread codes $C_1$ and $C_2$, and sets them in the correlators 43 and 44, respectively. At the correlators 43 and 44, the received signals are despread by the spread codes $C_1$ and $C_2$, and at the frame timing extraction circuit 47 into which they are entered through the demodulators 45 and 46, the temporal displacement of the two demodulated signals from the outputs of the demodulators 45 and 46 is measured, and notified to the control unit 41. For the respective signals demodulated by the demodulators 45 and 46, the timings are adjusted at the respective timing adjustment circuits 48 and 49 according to the signal from the control unit 41 such that the respective timings coincide. At the composition circuit 51, for the outputs of the demodulators 45 and 46 for which the timings are adjusted, the size of the reception levels in each bit measured by the reception level measurement circuits 52 and 53 are compared, and the data sequence is generated by selecting the larger one.

As a method of composition at the composition circuit 51, a case of a method for selection that with a higher reception level is selected in each bit has been shown in the present embodiment, but by using the reception level measurement circuits 52 and 53 which have functions for measuring and averaging the reception levels in frame units, and setting a unit of the selection composition to be each frame, a method for selecting a frame with a higher reception level in each frame can also be realized easily. Also, by changing the reception level measurement circuits 52 and 53 to the frame unit bit error rate measurement circuits, and setting a selection reference to be that with a lower bit error rate, a method for selecting a frame with a lower bit error rate can also be realized easily. Besides these, it is possible to compare and select in each bit or each frame by using an information representing the communication quality of the respective channels. Also, as a composition method, besides the selection composition as in the above, it is possible to adopt a method used for the diversity composition in general such as the maximum ratio composition, the equal gain composition, etc.

In general, at the wire transmission paths from the exchange station reaching to the base station $12_1$ and the base station $12_2$ have different delays, and the data sequence at the both sides of the base stations are out of synchronization. In addition, the base station transmissions in the radio section are also non-synchronous among the base stations. In such a situation, when a communication is made by using the identical spread code for the downward at a time of the simultaneous communications of the handover, they are going to be large interferences with each other as described before, and the communication quality is considerably degraded rather than improved. However, by using different spread codes as in this invention, it is possible to improve the quality significantly as they are independently demodulated and composed at the mobile station, regardless of the delays of the transmission paths and the non-synchronization among the base stations in the radio section.

Here, in the above described first embodiment, a case of the handover of the downward (from a base station to a mobile station) communication channel has been described as an example, but by placing a composition circuit at the base station or its upper level device, and composing the data signals received from the mobile stations at different cells in that base station at a time of the handover between the cells supported by the identical base station, or in the upper level device of these base stations at a time of the handover between cells supported by different base stations, it is possible to apply the combined use of the short spread code and the long spread code for the handover of the upward (from a mobile station to a base station) communication channel, similarly as in the downward handover. Moreover, it is possible to apply such a combined use of the short spread code and the long spread code not only to the communication channels but also to the upward and downward control channels.

As an example, it is possible to consider a case of adopting the following spread code configuration. Note that, in the following, the short spread code (common spread code) and the long spread code (identification spread code) will be referred as the short code and the long code, respectively.

In this example, for the purpose of increasing a number of spread codes that can be used in the system, while securing the secrecy effect, and in addition, making it possible to realize an autonomous distributed channel arrangement/allocation, the spread code is produced by combining a short code (a code for channel identification) which is common to the cells in 128 bit length in which 1 bit (0 or 1) is added to 127 bit Gold sequence with an upward long code (a code for base station identification) which is different for each base station or an upward long code (a code for mobile station identification) which is different for each mobile station, and a downward long code (a code for base station identification) which is different for each base station, which are produced by the method to be described below. Then, a perch channel (a channel for indicating a basic information, etc. to be used in a cell) as shown in FIG. 10, a downward control channel (a control channel from a base station with respect to a mobile station) and a downward communication channel (a communication channel from a base station with respect to a mobile station) as shown in FIG. 11, and an upward control channel (a control channel from a mobile channel with respect to a base station) and an upward communication channel (a communication channel from a mobile station with respect to a base station) as shown in FIG. 12 are constructed. Here, in FIGS. 10, 11, and 12, an expression G(X) represents a symbol sequence with a code length X, and an expression G(X, Y) represents a Y-th code of a symbol sequence with a code length X.

Figure 13A:
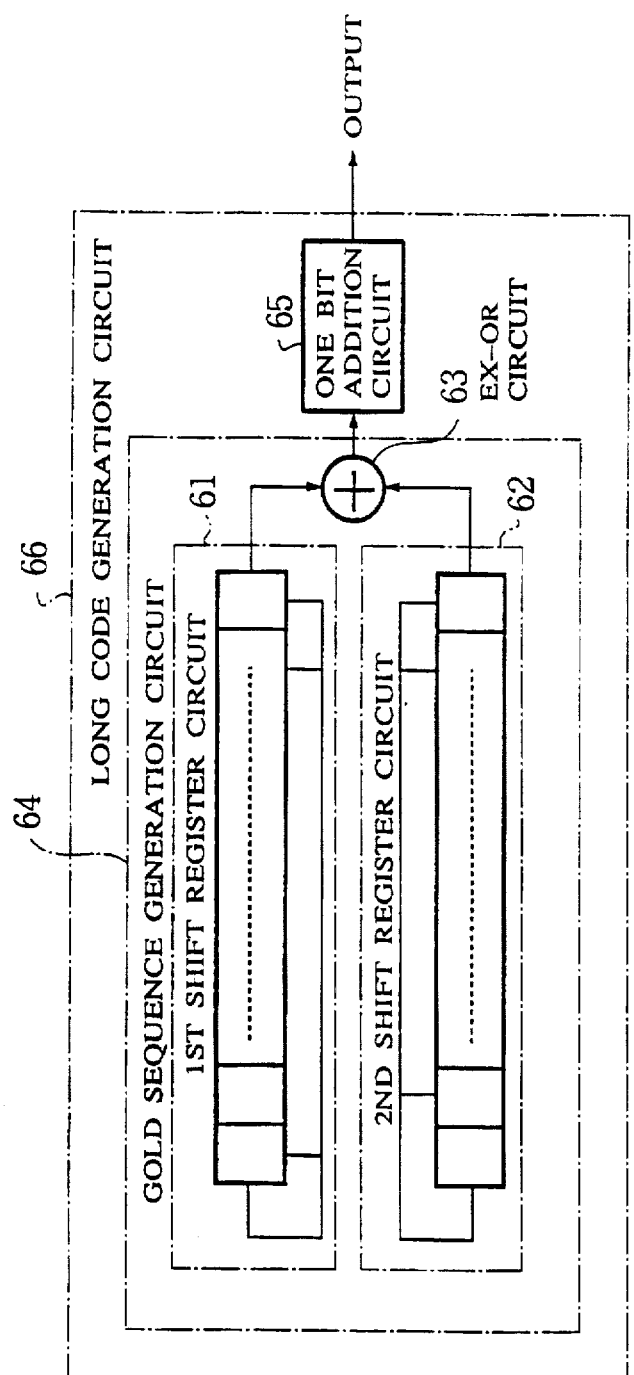
FIGS. 13A, 13B, and 13C are block diagrams showing a configuration of a long code generation circuit for generating long codes of FIGS. 11 and 12.

Here, the generation of the long code uses a long code generation circuit 66 as shown in FIG. 13A, which has a Gold sequence generation circuit 64 formed by a first shift register circuit 61 having 33 bits length, a second shift register circuit 62 having 33 bits length, and an EX-OR circuit 63 which adds the outputs of the fist and second shift register circuits 61 and 62, and a one bit addition circuit 65 which adds 0 or 1 at an end of the symbol sequence.

Then, at a time of generating the long code by this long code generation circuit 66, after the constituent elements of the long code are given to the first shift register circuit 61 as the initial value, while a predetermined fixed pattern is given to the second shift register circuit 62 as the initial value, these first and second shift register circuits 61 and 62 are subjected to the clock shift to generate the long code with a $2^{33}$ bit period.

Figure 13B:
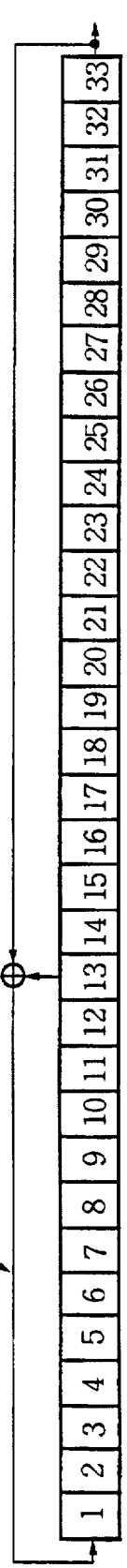
Figure 13C:
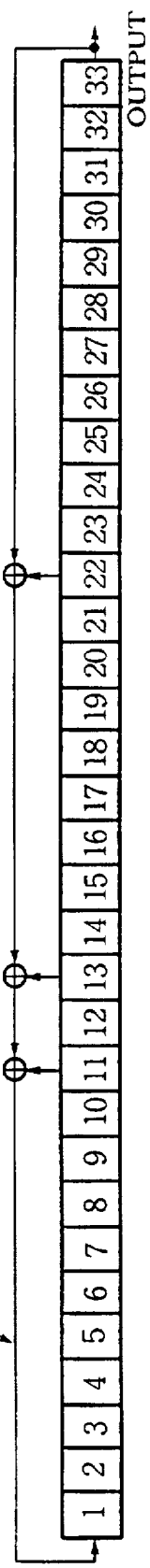

In this long code generation circuit 66, the first and second shift register circuits 61 and 62 have configurations as shown in FIGS. 13B and 13C, respectively. Namely, a number of stages of each shift register is 33 bits, and the first shift register takes the 13th and 33rd bits of the output of the EX-OR as an input for the 1st bit, and the second shift register takes the 11th, 13th, 22nd, and 33rd bits of the output of the EX-OR as an input for the 1st bit.

Figure 14:
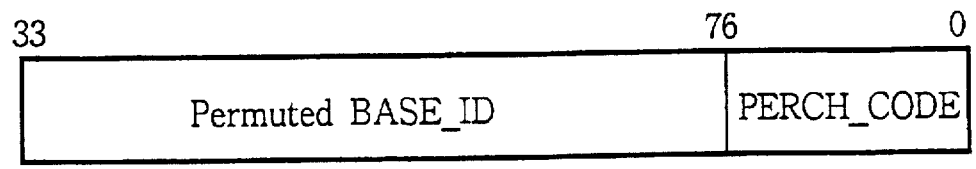
FIG. 14 is a diagram showing exemplary constituent elements of the long code used in downward control/communication channels of FIG. 11.
Figure 15:
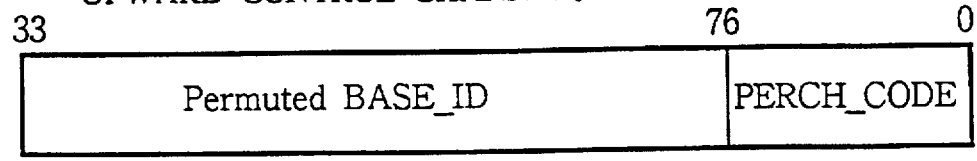
FIG. 15 is a diagram showing exemplary constituent elements of the long code used in an upward control channel of FIG. 12.
Figure 16:
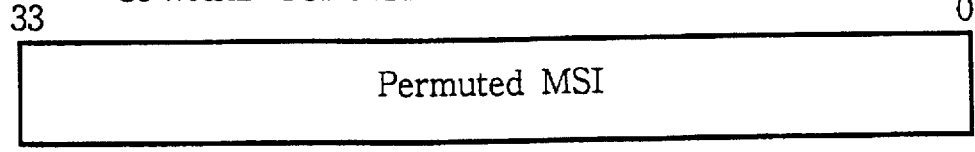
FIG. 16 is a diagram showing exemplary constituent elements of the long code used in an upward communication channel of FIG. 12.

In this case, as the constituent elements of the long code to be given to the first shift register circuit 61 as the initial value, the 33 bit code formed by 26 bit code (Permuted BASE ID) in which the base station identification number is set in a random order by a prescribed method and 7 bit code (PERCH CODE) obtained according to the perch channel number is used for the downward control channel and the downward communication channel as shown in FIG. 14, the 33 bit code formed by the 26 bit code (Permuted BASE ID) in which the base station identification number is set in a random order by a prescribed method and 7 bit code (PERCH CODE) obtained according to the perch channel number is used for the upward control channel as shown in FIG. 15, and the 33 bit code (Permuted MSI) in which the mobile station identification number is set in a random order by a prescribed method is used for the upward communication channel as shown in FIG. 16, for example.

Here, apart from the above described configuration, as the constituent elements of the long code, it suffices for the downward control and communication channels and the upward control channel to contain a thing that can identify the base station, and it suffices for the upward communication channel to contain a thing that can identify the mobile station.

Also, the base station identification number used as a constituent element of the long code is not limited to this and may be the other thing as long as it can uniquely determine each radio cell within the system.

In the following, using the spread code configuration of this example, the second and third embodiments of the present invention related to the synchronization of the channel spread codes in the CDMA mobile communication scheme will be explained in detail.

First, the second embodiment of the present invention related to the synchronization of the channel spread code in the CDMA mobile communication scheme using the spread code configuration of FIG. 10 to FIG. 16 described above will be explained in detail with references to FIG. 17 to FIG. 23.

Figures 17, 18:
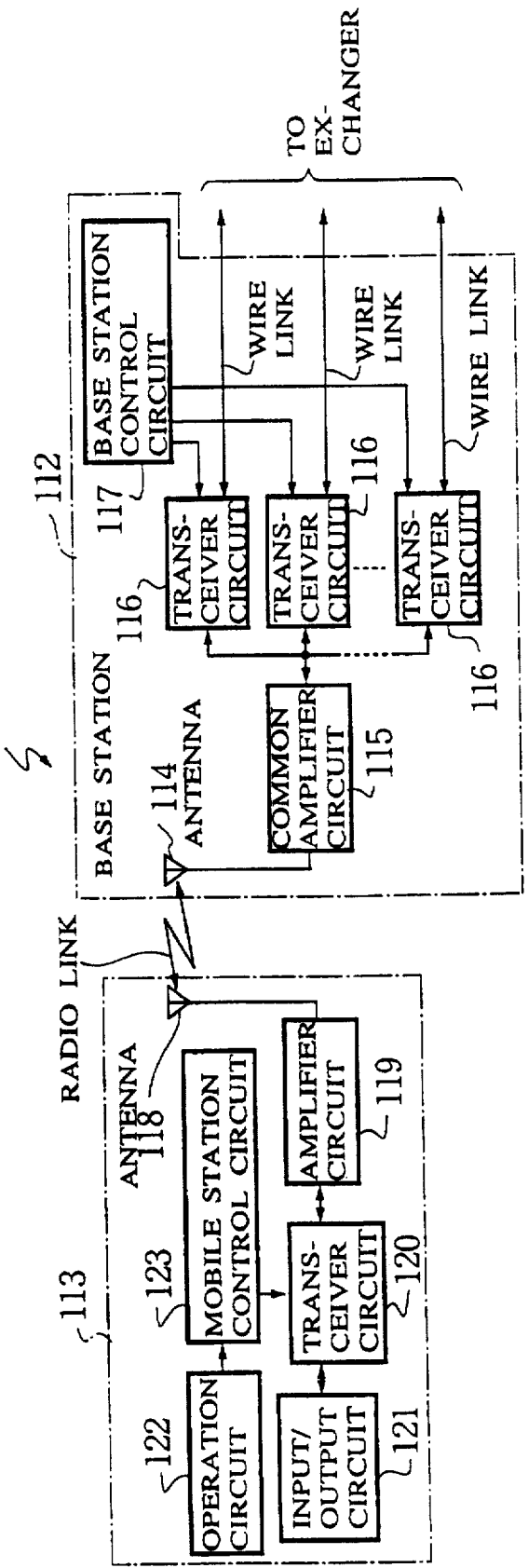
FIG. 17 is a block diagram showing a schematic configuration of a base station and a mobile station in a CDMA mobile communication system according to the second embodiment of the present invention.
FIG. 18 is a diagram showing an exemplary frame configuration for a perch channel in the CDMA mobile communication system of FIG. 17.

FIG. 17 shows a schematic configuration of a mobile communication system to which the channel spread code synchronization method in the CDMA mobile communication scheme according this second embodiment is applied.

A mobile communication system 111 shown in this FIG. 17 is equipped with a base station 112 provided in each cell constituting an area in which a communication is possible, and a mobile station 113 installed on an automobile or carried around, and at a time of starting a communication between the mobile station 113 and the base station 112, etc., the short code to be used in the communication between the mobile station 113 and the base station 112 is judged by sequentially measuring the reception level of the perch channel which is spread by using only the short code which is different for each base station 112 and comparing them, and then the connection control operation is carried out by establishing the synchronization of the downward control channel which is spread by using the short code and the long code between the mobile station 113 and the base station 112 by using the above described perch channel, and the communication using the upward communication channel and the downward communication channel are made.

In this case, for example, the perch channel is constructed as shown in FIG. 18, from a 2 bit preamble (PR) to be used for the clock reproduction, a 64 bit sink word (SW) to be a synchronization data, a 10 bit pilot word (PL) to be a reference, a 6 bit frame number (FRN) which is set to one of a values ranging from 0 to 49 which is necessary in constructing a super frame, a 33 bit long code phase data (LCPH) indicating a phase of the long code of the downward control channel and the upward control channel at a frame reference point, a 305 bit notification data (CAC) to be a control data, etc., a 22 bit collision control data (E) which is necessary in controlling collisions of signals in the upward control channel, a 6 bit tail bit (TA) indicating an end of an error control block, and an 8 bit power control data (TPC) for specifying a transmission power of the mobile station 113.

The above described base station 112 is equipped with an antenna 114 for carrying out transmission and reception of radio link signals, a common amplifier circuit 115 for amplifying the radio link signals transmitted or received through this antenna 114, a plurality of transceiver circuits 116 having the long code generation circuit 66 shown in FIG. 13, etc., for making a communication with an exchange station side through each wire link and carrying out transmission and reception processing for the radio link signals through the above described common amplifier 115, and a base station control circuit 117 for controlling transmission and reception operations of each of these transceiver circuits 116.

Then, the perch channel which is spread by using only the short code and the downward control channel which is spread by using the short code and the long code are transmitted all the times. Here, however, the constituent elements of the short code and the long code used in the downward control channel and the upward control channels are notified within the notification data of the perch channel. Then, at a time of starting the communication with the mobile station 113, etc., the connection control is carried out by using the downward control channel and the upward control channel which are spread by using the short code and the long code, and the communication with the above described mobile station 113 is made by using the upward communication channel and the downward communication channel.

Also, the mobile station 118 is equipped with an antenna for carrying out transmission and reception of radio link signals, an amplifier circuit 119 for amplifying the radio link signals transmitted or received through this antenna 118, a transceiver circuit 120 having the long code generation circuit 66 shown in FIG. 13, etc., for carrying out transmission and reception processing for the radio link signals through the above described amplifier circuit 119, etc., an input/output circuit 121 having a microphone, a speaker, etc., for making speech input and output, an operation circuit 122 having man-machine interfaces such as dial buttons and a display device, and a mobile station control circuit 123 for controlling the above described transceiver circuit 120 according to the operation content of this operation circuit 122.

Then, at a time of starting the communication with the base station, etc., the short code to be used in the communication with the base station 112 is determined by comparing the reception levels of the perch channel which is spread by using only the short code among a plurality of base stations, and judging the base station at the maximum reception level (this is set as the base station 112). After that, the above described perch channel is received, and the long code phase is read out from the LCPH, while the constituent elements of the short code and the long code in the downward and upward control channels are read out from the notification data, and the long code is generated at a phase read out from the long code constituent elements, and then the synchronization with the downward control channel is established by using this long code along with the short code. After that, the connection control is carried out in the downward control channel and the upward control channel which are spread by using the short code and the long code, and then the communication with the base station 112 is made by using the connection control in the upward communication channel and the downward communication channel.

Next, with references to FIG. 19 to FIG. 23, the operation of this second embodiment will be explained.

<A time of activation of mobile station 113 and a time of reception of downward control channel>

Figure 19:
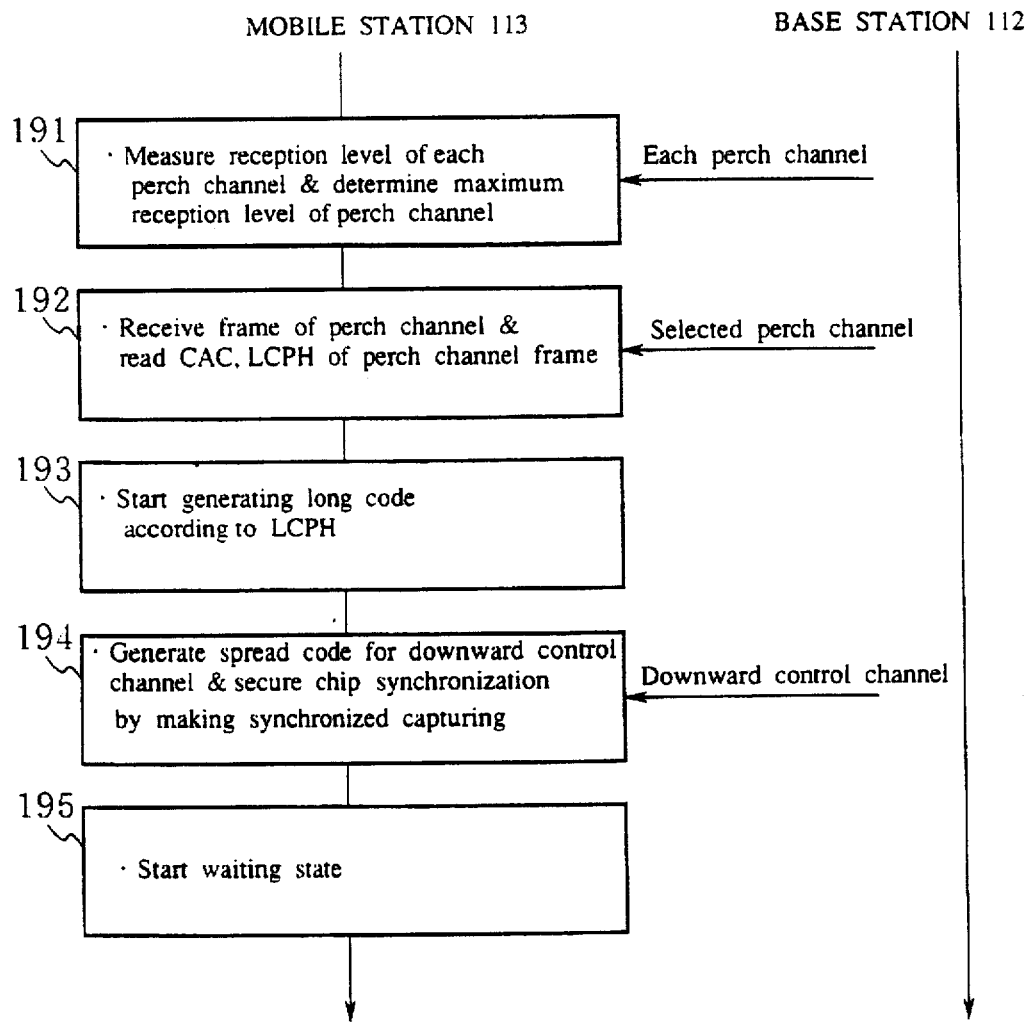
FIG. 19 is a sequence chart showing an operation at a time of activation of a mobile station and reception of a downward control channel in the CDMA mobile communication system of FIG. 17.

First, at a time of turning a power on at the mobile station 113 within one cell or at a time of carrying out a reception of the downward control channel, as shown in FIG. 19, by the mobile station control circuit 123 on the mobile station 113 side, a plurality of perch channel spread codes (short codes) written in the ROM (not shown) are sequentially switched and set to the transceiver circuit 120, the reception level of the perch channel from each cell is measured, and the perch channel with the maximum reception level among the above described perch channels is found out according to this reception level. (step 191)

After that, the transceiver circuit 120 is controlled by the mobile station control circuit 123 of the mobile station 113, and the frame of the perch channel is received by the perch channel spread code corresponding to the above described perch channel with the maximum reception level. Then, a base station number, a perch channel number, and a control channel configuration data in the notification data (CAC) are read out, while the long code phase data (LCPH) is read out in correspondence to the frame number (FRN). Here, however, in the control channel configuration data, the short codes for the upward and downward control channels are contained. (step 192)

Next, by the mobile station control circuit 123 in the mobile station 113, the code (permuted BASE ID) in which the base station number is set in a random order by a prescribed method and a code (PERCH CODE) obtained according to the perch channel number are set as the initial values in the first shift register circuit 61 of the long code generation circuit 66 in the transceiver 120, while the long code phase data (LCPH) is set, and the first and second shift register circuits 61 and 62 are shifted as much as a number of clocks indicated by this long code phase data (LCPH), and then the generation of the long code is started at a reference point (a timing (a) shown in FIGS. 22(A) and (B)) of the perch channel frame. At this point, prescribed initial values which are common to the base station 112 and the mobile station 113 are set up in the second shift register circuit 62. (step 193)

After that, by the transceiver circuit 120 on the mobile station 113 side, the spread code of the downward control channel is generated by multiplying the short code of the downward control channel and the long code generated by the long code generation circuit 66. In addition, the synchronized capturing is made by taking a correlation between the downward control channel signal and the spread code at the reception side. (step 194)

In this case, by the long code phase data (LCPH) of the perch channel as shown in FIGS. 22(A) and (B), an information that it becomes a reference point (a timing (a) shown in FIGS. 22(A) and (b)) of the perch channel frame, i.e., it becomes the long code for the first chip (a timing (a)) of the first symbol constituting the downward control channel, when the long code generation circuit 66 is shifted for how many clocks from the initial state, is indicated.

Then, the synchronization capturing (chip synchronization capturing) can be made easily with respect to the spread code of the downward control channel, by calculating a content of the long code at the (a) timing according to this long code phase data (LCPH) by the mobile station 113 side as shown in FIGS. 22(C) and (D), and taking the synchronization with respect to the downward control channel by generating the long code according to this calculation result.

After that, after the chip synchronization with respect to the received signal of the downward control channel is taken, it is possible to take the symbol synchronization and the frame synchronization sequentially, so that the content of the downward control channel is received by the transceiver circuit 120 on the mobile station 113 side, and it becomes a waiting state. (step 195)

<A time of upward control channel transmission>

Figure 20:
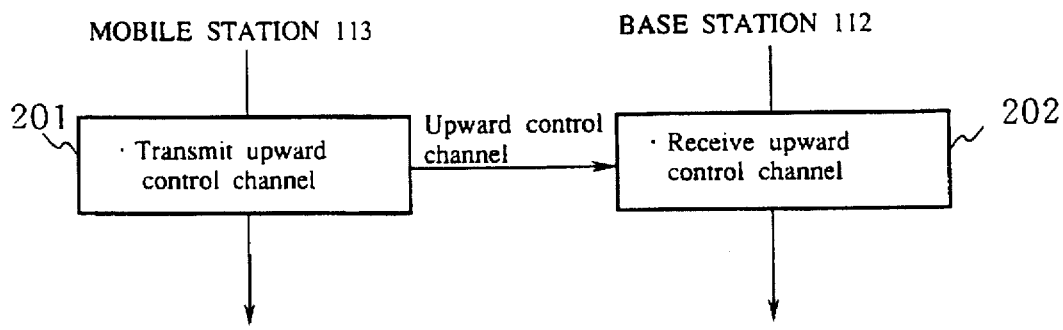
FIG. 20 is a sequence chart showing an operation at a time of transmission of an upward control channel in the CDMA mobile communication system of FIG. 17.
Figure 21:
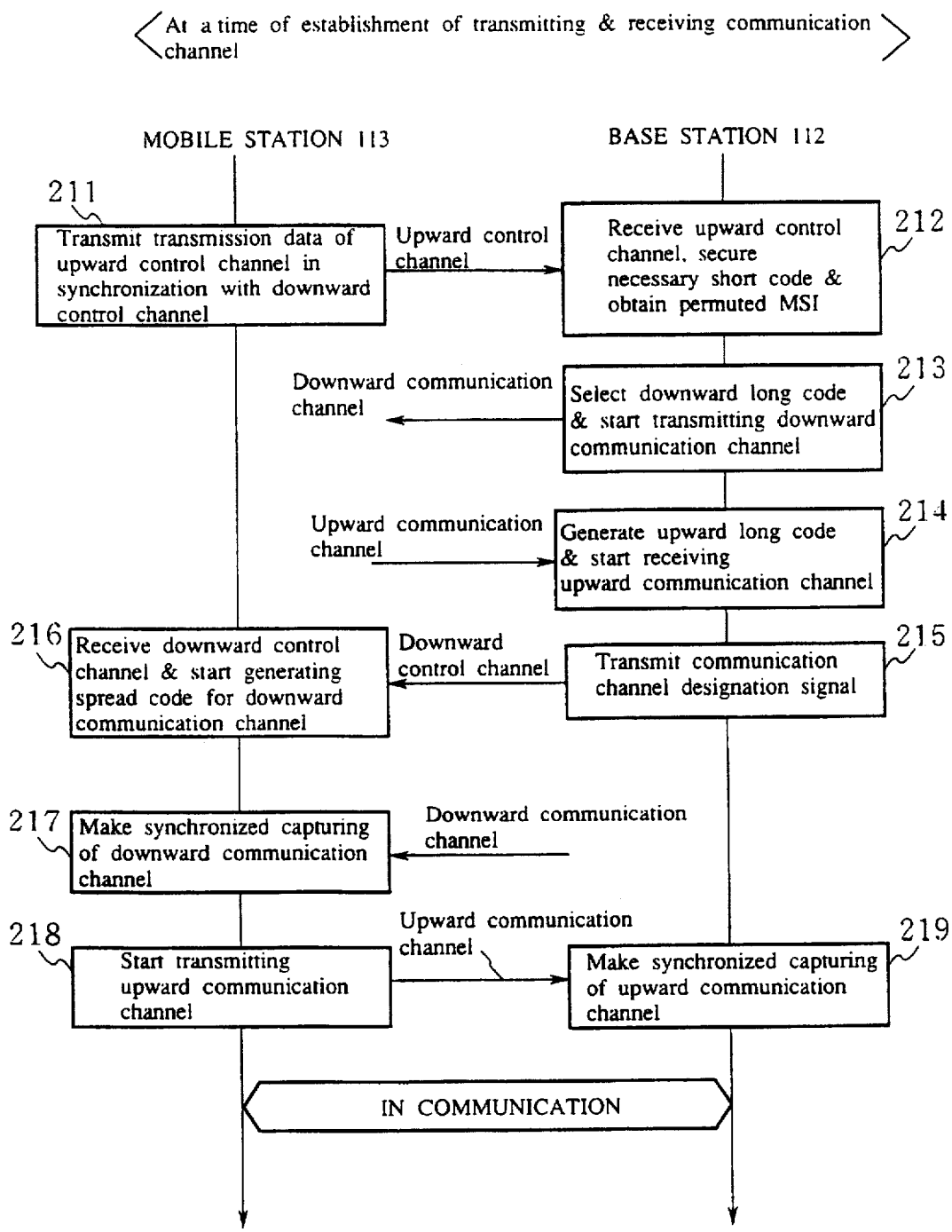
FIG. 21 is a sequence chart showing an operation at a time of establishment of transmitting and receiving communication channels in the CDMA mobile communication system of FIG. 17.

After that, at a time of transmitting the signals through the upward control channel from the mobile station 113 to the base station 112, as shown in FIG. 20, the upward long code is generated at the long code phase which is synchronized with the long code phase of the downward control channel by the transceiver circuit 120 on the mobile station 113 side, and the signal of the upward control channel to be the transmission target as the short code is used is spread, and transmitted as shown in FIG. 22(E). (step 201)

Then, by the transceiver circuit 116 on the base station 112 side, the despreading is carried out by using the above described long code and short code as shown in FIG. 22(F), and the synchronized capturing is made. At this point, the upward long code phase is based on the downward long code phase as described above, so that the upward long code phase to be used at a time of the base station reception can be generated easily, and the synchronized capturing can be made easily. In this manner, the signal of the upward control channel is received. (step 202)

<A time of transmitting and receiving communication channel establishment>

Next, at a time of establishing a communication channel by carrying out transmitting and receiving connection control, the signal of the upward control channel is generated as the long code phase is adjusted in synchronization with the signal of the downward control channel by the mobile station 113, while a number of channels, a mobile station number, etc. necessary for a communication which are to be the transmission data in this upward control channel are notified to the base station 112 side. (step 211)

Then, by the base station 112, as many short codes as a number of necessary channels are secured according to the transmission data from the above described mobile station 113 side, and then the 33 bit code (Permuted MSI) in which the mobile station identification number is set in a random order according to a prescribed method is generated. (step 212)

After that, at one base station 112, the identical long code is used in the downward within the identical base station 112 (within the cell), so that the same long code as the long code of the downward control channel is selected as the long code of the downward communication channel by the transceiver circuit 116 on the base station 112 side, and moreover used for the spreading at the identical phase. The timing relationship in this case is shown in FIG. 23. At the perch channel, the long code phase corresponding to (a) is notified, and the mobile station 113 can learn the phase of (a) in FIGS. 23(B) and (C). By means of this, the mobile station 113 can demodulate and decode the downward data signal which is spread by the long code and the short code. In this manner, from the base station 112, the data of the downward communication channel is modulated and transmitted according to the selected long code and short code. (step 213)

After that, by the base station 112, the 33 bit code (permuted MSI) in which the mobile station identification number is set in a random order by a prescribed method is set to the first shift register circuit 61 of the long code generation circuit 66 in the transceiver 116, and then, the shifting of the first and second shift register circuits 61 and 62 at the phase synchronized with the long code phase of the above described downward communication channel is started and the long code for the upward communication channel is generated, while the reception of the upward communication channel is started by using this upward long code and the short code. (step 214).

Next, a frequency, upward and downward short codes, etc., which become a channel designation data for specifying the upward and downward communication channels are collected together by the transceiver circuit 116 of the base station 112, and this is notified as the channel designation signal to the transceiver circuit 120 on the mobile station 113 side through the downward control channel. (step 215)

Then, by the transceiver circuit 120 of the mobile station 113, the generation of the downward long code is started at the same timing as the downward control channel according to the channel designation signal from the above described base station 112 side, and in addition, the reception of the downward communication channel is carried out by using this downward long code and the short code, and the synchronized capturing of the downward communication channel is made. (step 217)

Next, by the transceiver circuit 120 of the mobile station 113, when the synchronization of the downward communication channel is taken, the 33 bit code (permuted MSI) in which the mobile station identification number is set in a random order according to a prescribed method is set to the first shift register circuit 61 of the long code generation circuit 66 in the transceiver circuit 120, and then, the shifting of the first and second shift register circuits 61 and 62 at the phase synchronized with the long code phase of the above described downward communication channel is started and the long code for the upward communication channel is generated, while the signal of the upward communication channel is generated by using this upward long code and the short code, and this is transmitted by being adjusted to the frame timing and the long code phase of the above described downward communication channel. (step 218)

After that, by the transceiver circuit 116 of the base station 112, the synchronized capturing of the upward communication channel is made by using the upward long code and the short code, and it enters into a state of communication with the above described mobile station 113. (step 219)

As described, in this second embodiment, it is made such that, at a time of starting the communication between the mobile station 113 and the base station 112, etc., the short code to be used in the communication between the mobile station 113 and the base station 112 is selected by using the perch channel which is spread by using only the short code, and then the synchronization of the downward control channel which is spread by using the short code and the long code is established between the mobile station 113 and the base station 112 by using the long code phase data (LCPH) of the above described perch channel, and the communication is made by using the downward control channel, the upward control channel, the upward communication channel, and the downward communication channel which are spread by using the short code and the long code, so that even when each spread code becomes long, the phase of the long code obtained by the long code generation circuit 66 and the phase of the long code which is spreading the received signal can be made to coincide in short time, and by means of this, it is possible to carry out the establishment and the switching of the communication channel smoothly while drastically increasing a number of communication channels between the mobile station 113 and the base station 112.

It is noted that, in the above described embodiment, it has been explained by assuming the phase data of the long code notified by the perch channel as the long code phase in the symbol at a top of the next frame, but there is no need to limit it to this, and it can be realized at any timing as long as it is a timing predetermined between the base station 112 and the mobile station 113.

Also, it has been explained for a case using the Gold symbol having a code length of 128 bit in which 1 bit is added to 127 bits as the short code, and the gold symbol having a code length of $2^{33}$ bits in which 1 bit is added to $2^{33}-1$ bits as the long code, but regarding the code length, it may be the code length other than these as long as they satisfy the requested conditions such as a number of simultaneously communicating stations in the CDMA mobile communication system. Also, it may be fine to use any symbol other than the Gold symbol as long as it is a symbol which satisfies the requested conditions.

Next, the third embodiment of the present invention related to the synchronization of the channel spread code in the CDMA mobile communication scheme using the spread code configuration of FIG. 10 to FIG. 16 described above will be explained in detail with references to FIG. 24 to FIG. 29.

Figure 24:
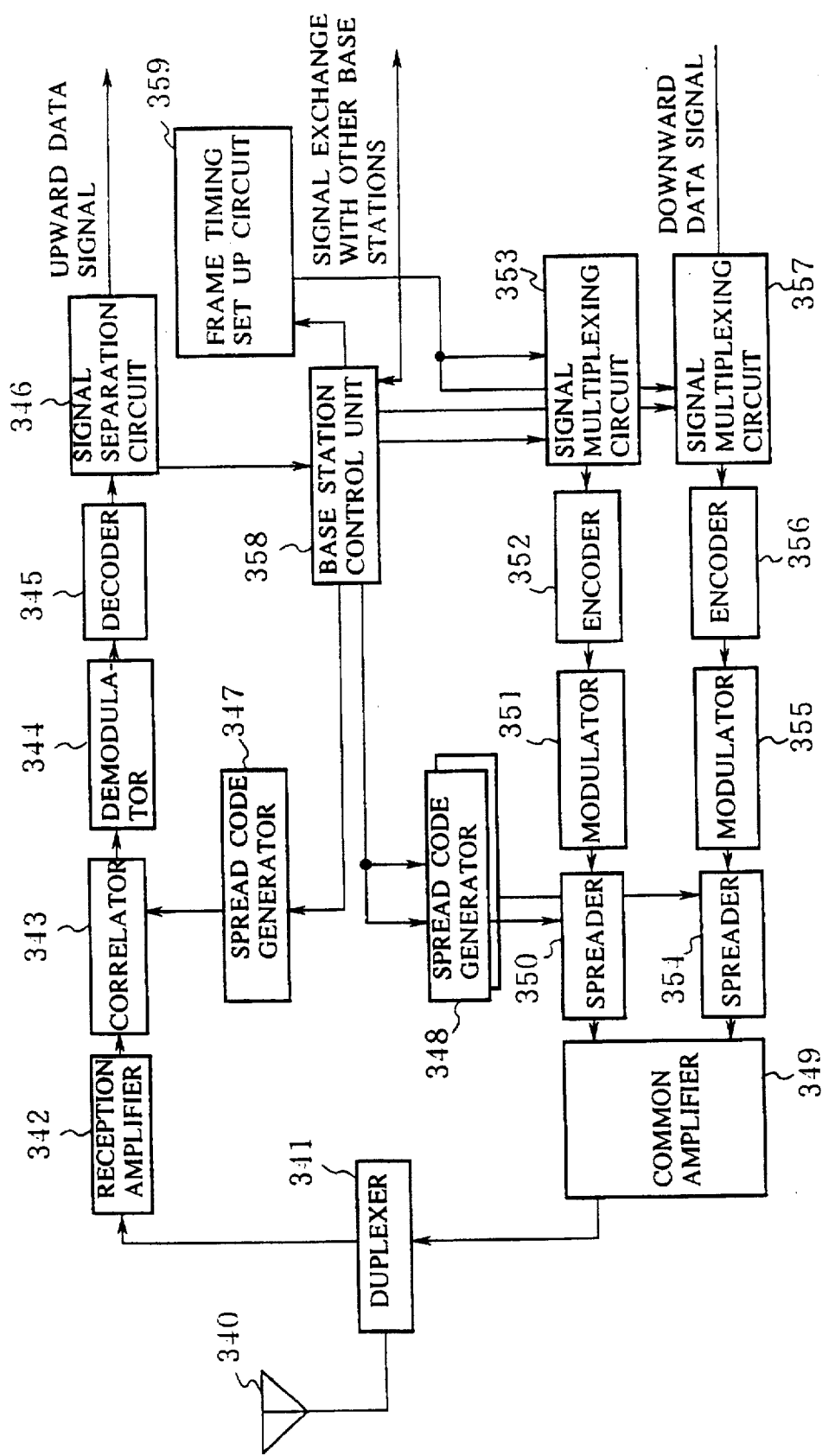
FIG. 24 is a block diagram showing a configuration of a base station in a CDMA mobile communication system according to the third embodiment of the present invention.
Figure 25:
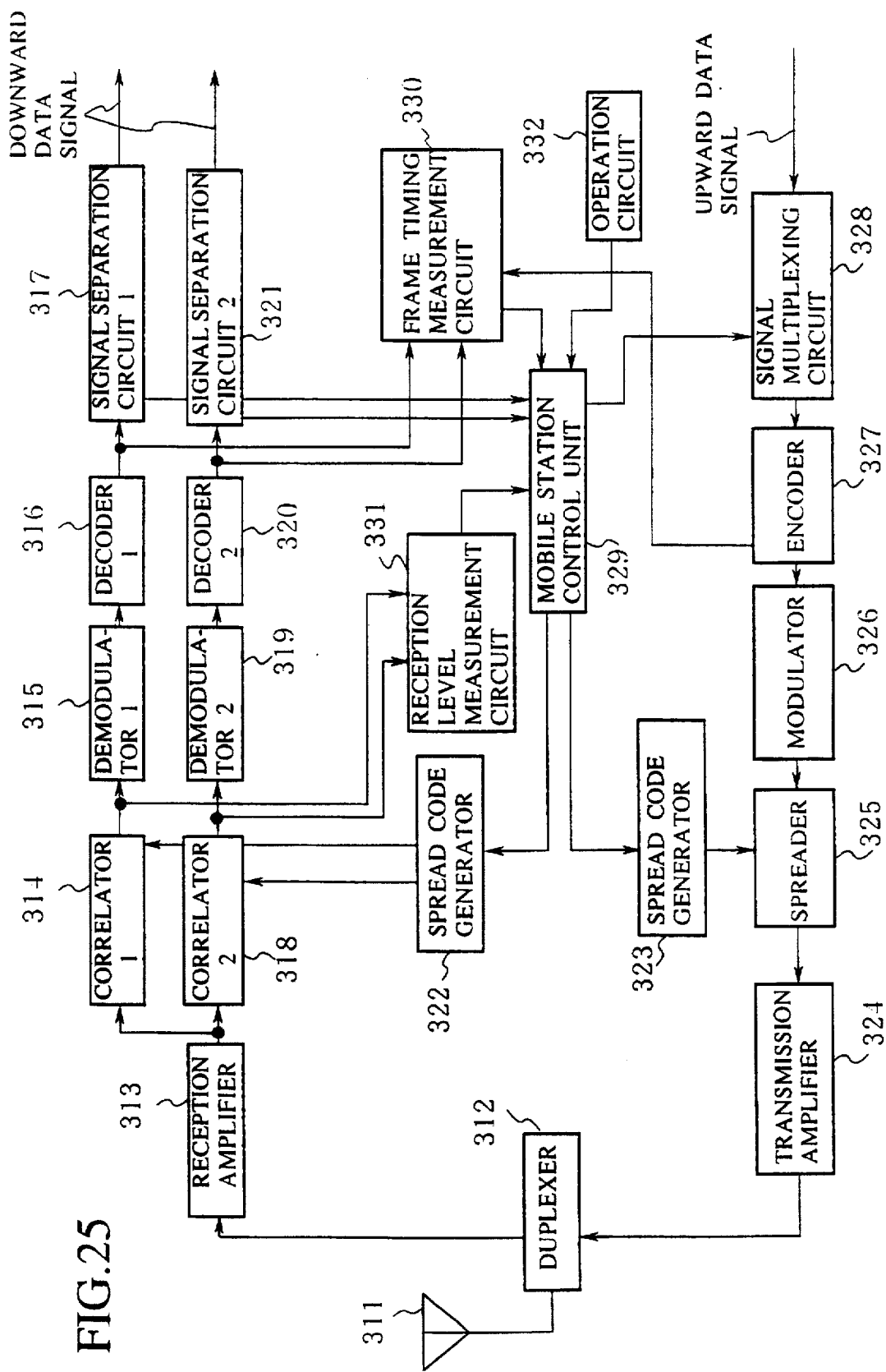
FIG. 25 is a block diagram showing a configuration of a mobile station in a CDMA mobile communication system according to the third embodiment of the present invention.

FIGS. 24 and 25 show exemplary configurations of the base station and the mobile station, respectively, in the mobile communication system to which the channel spread code synchronization method in the CDMA mobile communication scheme according this third embodiment is applied.

In FIG. 24, 340 is an antenna, 341 is a duplexer for distributing a received signal from the antenna 340 to a reception amplifier 342 while distributing an output of a common amplifier 349 to the antenna 340,342 is a reception amplifier for amplifying the received signal, 343 is a correlator for taking a correlation of the amplified received signal and a spread code generated by a spread code generator 347, 344 is a demodulator for demodulating an output of the correlator 343, 345 is a decoder for decoding an output of the demodulator 344, and 346 is a signal separation circuit for judging a frame configuration of an output of the decoder 345, and separately outputting the respective frame constituent elements.

Also, 347 and 348 are spread code generators which have the long code generation circuit 66 shown in FIG. 13, etc., and which generate the spread codes for the upward and downward data signals, respectively, as the configuration data and the generation initial phases of the short code and the long code are specified from a base station control unit 358, 353 is a signal multiplexing circuit for generating a frame by multiplexing the control data, etc., transferred from a base station control unit 358, and making an output at a timing specified from a frame timing set up circuit 359, 352 is an encoder for encoding the multiplexed control signals, 351 is a modulator for modulating an output of the encoder 352, and 350 is a spreader for spreading an output of the modulator 351 by multiplying the spread code generated by the spread code generator 348.

Also, 357 is a signal multiplexing circuit for generating a frame by multiplexing the control data, etc., transferred from a base station control unit 358 and the downward data signal, and making an output at a timing specified from a frame timing set up circuit 359, 356 is an encoder for encoding the multiplexed control signals, 355 is a modulator for modulating an output of the encoder 356, 354 is a spreader for spreading an output of the modulator 355 by multiplying the spread code generated by the spread code generator 348, and 349 is a common amplifier for amplifying outputs of the spreaders 350 and 354 and outputting them to the duplexer 341.

In this case, the spreader 350 to the signal multiplexing circuit 353 are used for the perch channel and the control channel transmission, while the spreader 354 to the signal multiplexing circuit 357 are used for the communication channel transmission.

Also, 359 is a frame timing set up circuit for adjusting transmission timing by setting the frame timing specified from a base station control unit 358 to the signal multiplexing circuits 353 and 357, and 358 is a base station control unit which has a function to read out the control signal from the signal separation circuit 346, a function to exchange the long code phase data and the frame time difference data with the other base stations, a function to set up the short code, the long code, and their initial phases to the spread code generators 347 and 348, a function to output the control signal to the signal multiplexing circuits 353 and 357, etc.

Here, in FIG. 24, a case in which the channel for communication is one for upward and one for downward is shown, but it is possible to support a plurality of communication channels by providing a system from the spreader 354 to the signal multiplexing circuit 357 and a system from the reception amplifier 342 to the signal separation circuit 346 in plurality. In addition, a configuration in which the upward/downward control channel containing the perch channel (only downward) is also one is shown, but it is possible to support a plurality of the perch channels and the upward/downward control channels by providing a system from the spreader 350 to the signal multiplexing circuit 353 in plurality.

Also, in FIG. 25, 311 is an antenna, 312 is a duplexer for distributing a received signal from the antenna 311 to a reception amplifier 313 while distributing an output of a transmission amplifier 324 to the antenna 311, 313 is a reception amplifier for amplifying the received signal, 314 is a first correlator for taking a correlation of the amplified received signal and a spread code generated by a spread code generator 322, 315 is a first demodulator for demodulating an output of the first correlator 314, 316 is a first decoder for decoding an output of the first demodulator 315, and 317 is a first signal separation circuit for judging a frame configuration of an output of the first decoder 316 and separately outputting the respective frame constituent elements.

Also, 322 is a spread code generator which has the long code generation circuit 66 shown in FIG. 13, etc., and which generates the spread code for the downward data signals as the configuration data and the generation initial phase of the short code and the long code are specified from a mobile station control unit 329, separately for the first correlator 314 and the second correlator 318, 318 is a second correlator for taking a correlation of the amplified received signal and the spread code generated by the spread code generator 322, 319 is a second demodulator for demodulating an output of the second correlator 318, 320 is a second decoder for decoding an output of the second demodulator 319, and 321 is a second signal separation circuit for judging a frame configuration of an output of the second decoder 319 and separately outputting the respective frame constituent elements.

In this case, a reason for providing a plurality of reception systems of the first correlator 314 to the first signal separation circuit 317 and the second correlator 318 to the second signal separation circuit 321 is that the simultaneous receptions for the purpose of the soft handover are to be carried out, and a plurality of downward data signals are composed into one data signal by a signal composition circuit not shown in the figure.

Also, 323 is a spread code generator which has the long code generation circuit 66 shown in FIG. 13, etc., and which generates the spread code for the upward data signals as the configuration data and the generation initial phase of the short code and the long code are specified from a mobile station control unit 329, 328 is a signal multiplexing circuit for generating a frame by multiplexing the control data, etc., transferred from a mobile station control unit 329 and the upward data signal, 327 is an encoder for encoding the multiplexed control signal, 326 is a modulator for modulating an output of the encoder 327, 325 is a spreader for spreading an output of the modulator 326 by multiplying the spread code generated by the spread code generator 323, and 324 is a transmission amplifier for amplifying an output of the spreader 325 and outputting it to the duplexer 312.

Also, 332 is an operation circuit having dial switches, etc., 331 is a reception level measurement circuit for detecting a reception level of a peak of the outputs of the first and second correlators 314 and 318, 330 is a frame timing measurement circuit for measuring a frame timing for the received signal from the output of the first and second decoders 316 and 320 and a transmission frame timing from the encoder 327, and notifying them to a mobile station control unit 329, and 329 is a mobile station control unit which has a function to read out the control signals from the first and second signal separation circuits 317 and 321, a function to set up the short code, the long code, and their initial phases to the spread code generators 322 and 323, a function to output the control signals to the signal multiplexing circuit 328, a function to receive the measured values from the frame timing measurement circuit 330 and the reception level measurement circuit 331, a function to carry out calculations to obtain a time difference and a phase difference as described later, etc.

Next, using FIG. 26 to FIG. 29, the operations of the base station and the mobile station at a time of the handover between cells will be explained.

First, the base station is transmitting the perch channel by using the transmission system of the spreader 350 to the signal multiplexing circuit 353 of FIG. 24. Here, it is assumed that the perch channel has a configuration similar to that shown in FIG. 18 in the above described second embodiment.

Figure 26:
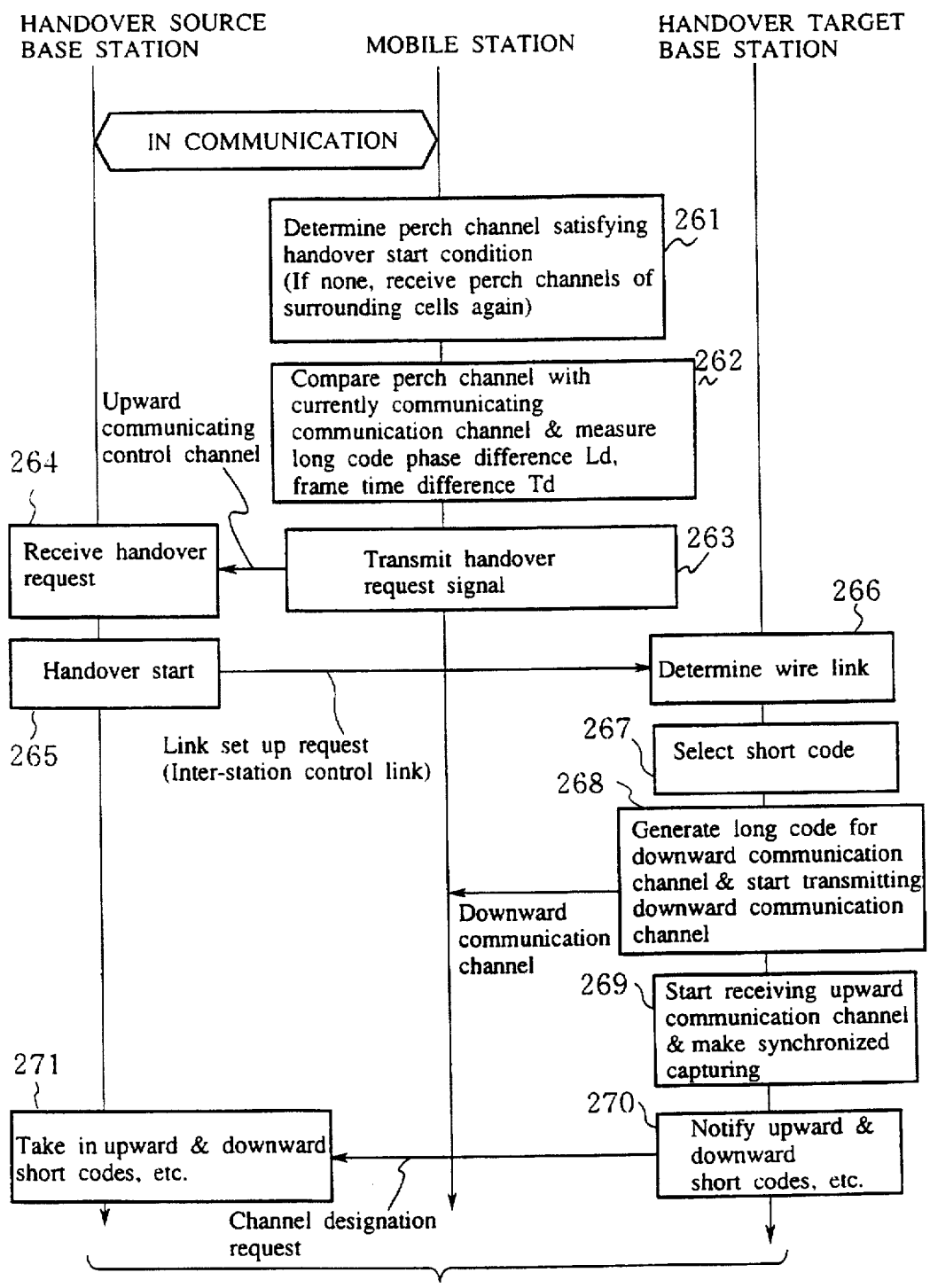
FIG. 26 is a sequence chart showing a first half of an operation at a time of the handover in the CDMA mobile communication system of FIGS. 24 and 25.
Figure 27:
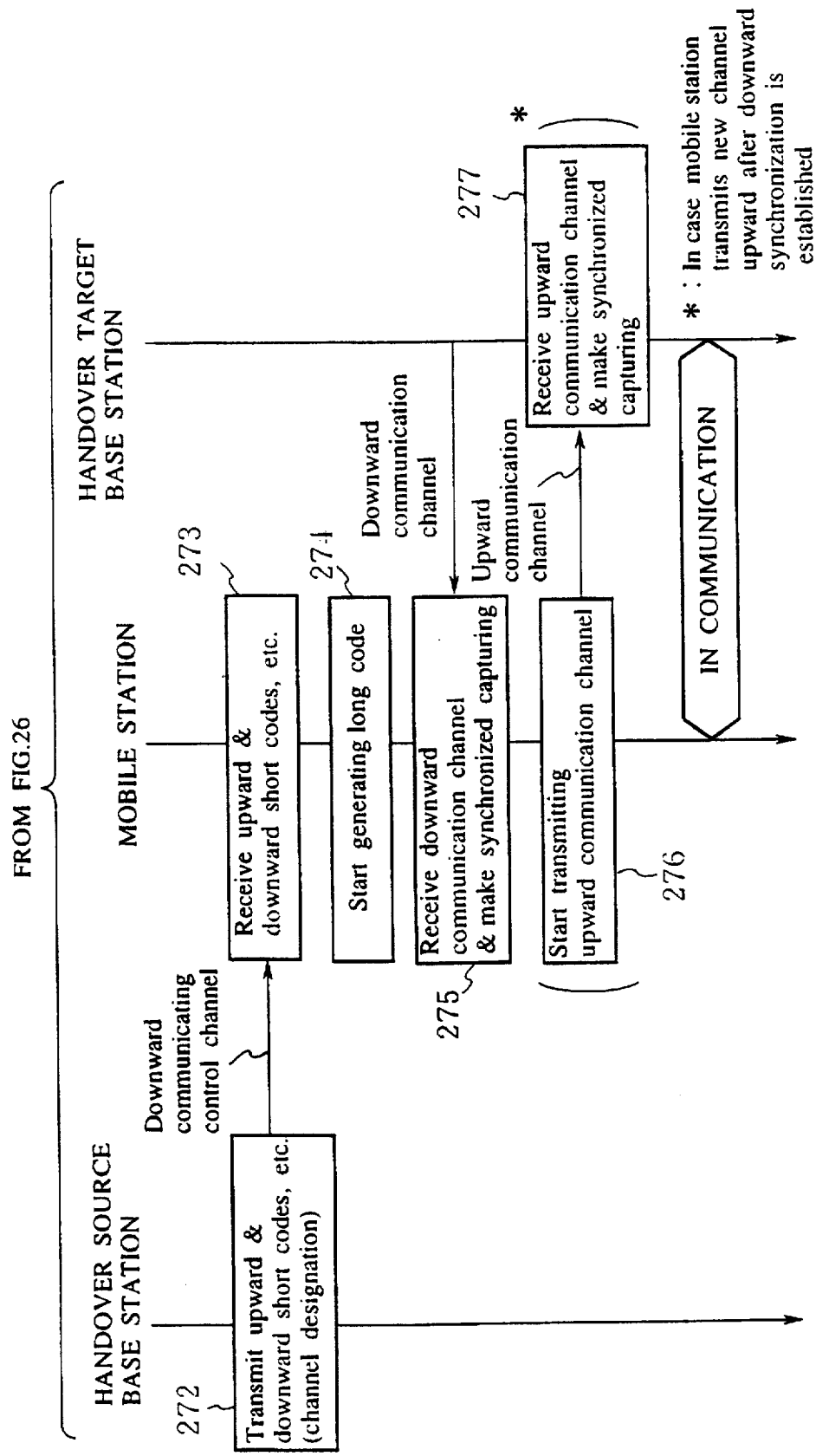
FIG. 27 is a sequence chart showing a second half of an operation at a time of the handover in the CDMA mobile communication system of FIGS. 24 and 25.

Also, supposing that the mobile station is in communication by the reception system of the first correlator 314 to the first signal separation circuit 317 shown in FIG. 25, at a time of carrying out the handover operation by detecting a cell transition due to the movement of the mobile station, etc., this is done by the procedure shown in FIG. 26 and FIG. 27.

The mobile station finds out the spread code with the maximum reception level by making the mobile station control unit 329 to sequentially set the spread codes (short code) of the perch channels of the surrounding cells, which are either written in the ROM (not shown) or notified from the base station, into the spread code generator 322, and making the reception level measurement circuit 331 to measure the reception level by using the system which uses the second correlator 318 which is not used for the communication. Then, whether to activate the transition target cell and the handover or not is determined according to the reception level and the spread code detected by this operation. (step 261)

In a case there is no perch channel which satisfies the handover activation condition, the reception of the perch channels of the surrounding cells is repeated once again.

Now, the operation in a case the handover is activated will be explained.

First, at the mobile station, the communication with the handover source base station is continued by the reception system of the first correlator 314 to the first signal separation circuit 317, and in parallel to this, the reception of the perch channel of the handover target base station is carried out by the reception system of the second correlator 318 to the second signal separation circuit 321.

In this case, the corresponding spread code is set up to the spread code generator 322 from the mobile station control unit 329, the perch channel is received by taking the correlation by this spread code, and the base station identification number, the perch channel number, the control channel configuration data, etc., in the notification data portion (CAC) constituting this perch channel frame are read out, while the long code phase data (LCPH) is read out. Here, the long code phase data is indicating the long code phase at a timing to be reference, i.e., a value indicating how much it has been shifted from the long code initial state, and in FIG. 28 for example, it is indicating a phase at a timing of (a), i.e., at a top of the next frame. Therefore, when the value of the long code phase data is P1, at a top of the next frame, it is in a state which has been shifted for a value P1 from the long code initial state.

Next, the mobile station measures a time difference Td between a timing (a) corresponding to the received long code phase data and a top timing (b) of a frame closest to the currently communicating upward communication channel, as shown in FIGS. 28(A) and (B), by using the frame timing measurement circuit 330. Also, at this point, the mobile station control unit 329 reads out the phase data at a point (b) of the long code which is used in the currently communicating upward communication channel from the spread code generator 323 and sets this as P2. Then, by obtaining a difference P2–P1 between this and the long code phase data value P1, a difference of the long code phases at a point (a) of the perch channel and a point (b) of the currently communicating upward communication channel is obtained as a difference of clock numbers, and this value is set as Ld. (step 262)

In this case, the phase of the long code is identical in a plurality of channels used at the base station, and in a case the upward transmission is carried out in synchronization with the downward long code phase, Ld is going to represent the long code phase difference between the handover source base station and the handover target base station.

Next, the handover request signal is generated by the mobile station control unit 329. This handover request signal contains data elements of the handover target base station identifier, the mobile station identifier, the frame time difference Td described above, the long code phase difference Ld, etc. Then, the handover request signal is transmitted to the currently communicating base station through the control channel in communication. (step 263)

Next, when the handover request signal is received (step 264), the handover source base station reads out its content at the base station control unit 358, judges the handover target base station from the handover target base station identifier, and transmits the link set up request signal containing data elements of at least the required number of channels, the mobile station identifier, the frame time difference Td, the long code phase difference Ld, etc., to this handover target base station through the control lines between the base stations. (step 265)

Then, at the handover target base station which received this, as many wire links as the required number of channels, and the spread codes (short codes) for the upward and downward communications are selected (steps 266 and 267), while after the communication channels are allocated as shown in FIG. 29(A) and (B), the downward communication long code is generated by setting the downward communication short code in the spread code generator 348 by the base station control unit 358, and the transmission of the downward communication channel is carried out. (step 268)

At this point, the long code phase and the frame timing are as follows. Namely, assuming that the transmission long code phase of the mobile station is identical before and after the handover, the long code phase difference Ld notified from the handover source base station is the long code phase difference between the base stations at a reference timing, so that it can be seen that, with reference to the perch channel transmission of the own base station, it is a point at which the long code phase at a timing which is ahead by as much as the frame time difference Td is a point at which the phase is ahead by as much as the long code phase difference Ld.

By means of this, the transmission long code phase of the mobile station at that timing can be seen, so that by generating the upward communication long code by setting that to the spread code generator 347, the reception of the upward communication channel is carried out in a short synchronized capturing period, and the synchronized capturing is made. (step 269)

Also, the short codes of the upward and downward channels, etc., which are selected at the handover target base station are transmitted to the handover source base station through the control line in a form of being contained in the channel designation request signal (steps 270 and 271), and after that, they are notified from the handover source base station to the mobile station by the channel designation signal (steps 272 and 273).

Then, at the mobile station, the initial state of the shift register of the long code generation circuit 66 within the spread code generator 322 is set up from the handover target base station identification number and the perch channel spread code, and in addition, the long code phase (a number of clocks since the initial state) at a timing for making the synchronized capturing is calculated from the notified long code phase data, and the long code shifted from the initial state is generated. (step 274)

The despreading is carried out by the spread code in which this long code and the specified downward communication short code are multiplied together, and the synchronized capturing is made. By means of this, the reception of the downward communication in a short synchronized capturing period becomes possible. (step 275)

Here, a case of carrying out the handover by the identical spread code for the upward has been described in the above, but in a case the spread codes are changed for both upward and downward, after the synchronization establishment for the downward communication channel, the transmission of the upward communication channel is carried out (step 276), and this is received by making the synchronized capturing at the handover target base station. (step 277)

As described, in this embodiment, in a case the mobile station in communication carries out the handover, it is made such that the displacement between the frame of the currently communicating communication channel and the frame of the perch channel which is used at the base station located within a moving target cell is measured, and this measurement result is transmitted to the handover target base station through the handover source base station, and the long code phases of the downward communication channel transmitted from this handover target base station and the upward communication channel received by the above described handover target base station, etc., are adjusted, so that even when each spread code becomes long, the phase of the spread code obtained by the long code generation circuit and the phase of the spread code which is spreading the received signal can be made to coincide in short time, and by means of this, it is possible to carry out the switching of the communication channel smoothly at a time of the handover while drastically increasing a number of communication channels between the mobile station and the base station.

Also, by modifying the above described third embodiment, it may be fine to generate the frame of the downward communication channel at the same timing as the upward communication channel frame of the handover source base station and transmit this at the handover target base station for example.

Here, by applying the above described third embodiment, for the purpose of improving the VOX effect at the handover target base station, it is possible to set offsets randomly to the frames of the downward communication channel of the handover target base station with respect to the frames of the perch channel of the handover source base station, transmit these offset values, the upward and downward short codes, the frequency, etc., to the mobile station sequentially through the interstation control line and the handover source base station, and set offsets to the frames of the upward communication channel transmitted from this mobile station, and by doing this, it is possible to increase the statistical multiplexing effect at a time of the VOX control, at the cell in which the handover target base station is existing. Also, such a scheme will be effective in improving the VOX effect in a general VOX control as well.

In the following, the fourth embodiment of the present invention related to a scheme for utilizing the reduction of an amount of interference in conjunction with such a VOX control to an increase of the system capacity will be explained in detail with references to FIG. 30 to FIG. 32.

First, a case of downward (a signal transmission from a base station to a mobile station) will be explained.

Figure 30:
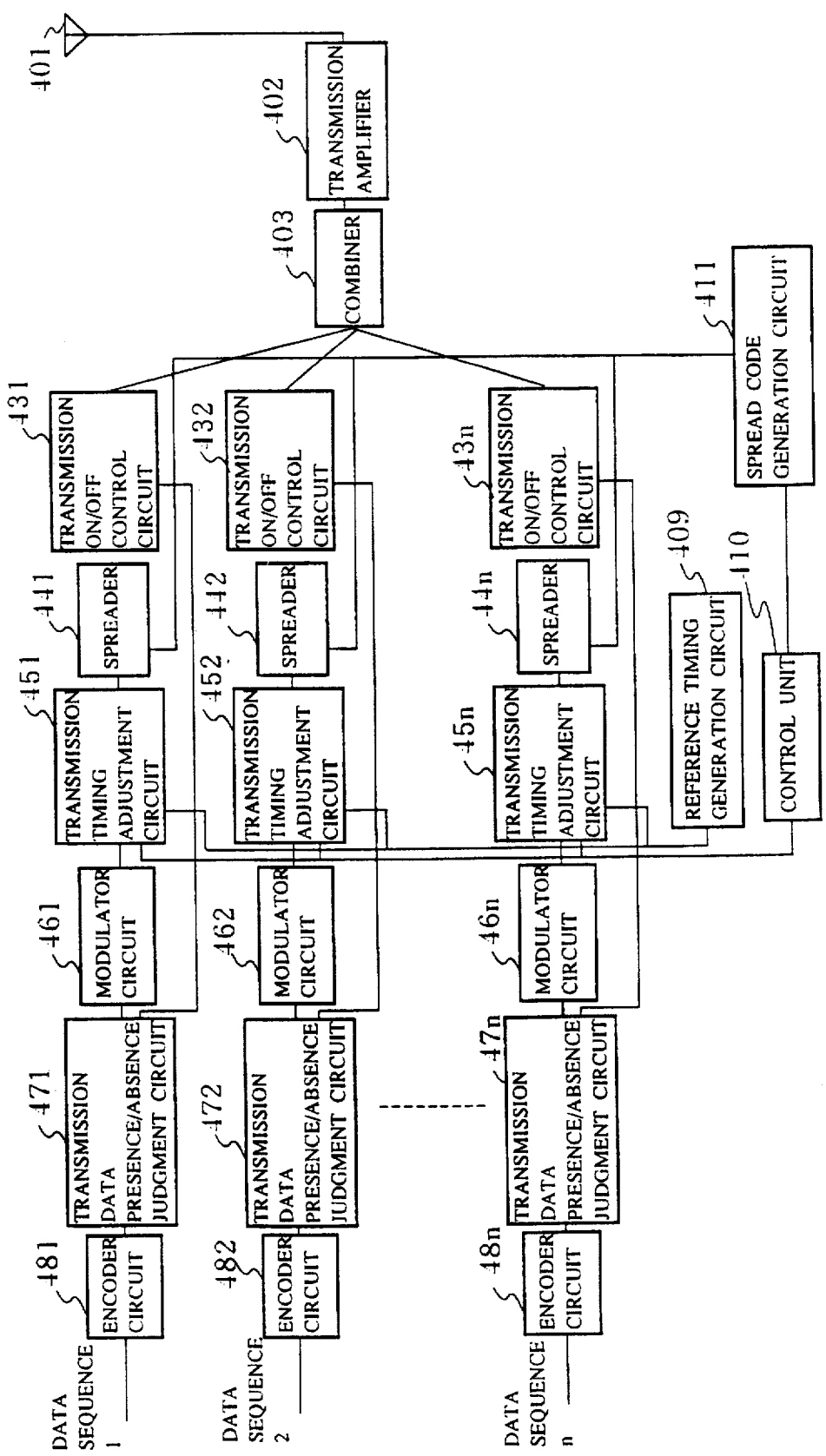
FIG. 30 is a block diagram showing a configuration of a base station in a CDMA mobile communication system according to the fourth embodiment of the present invention.
Figure 31:
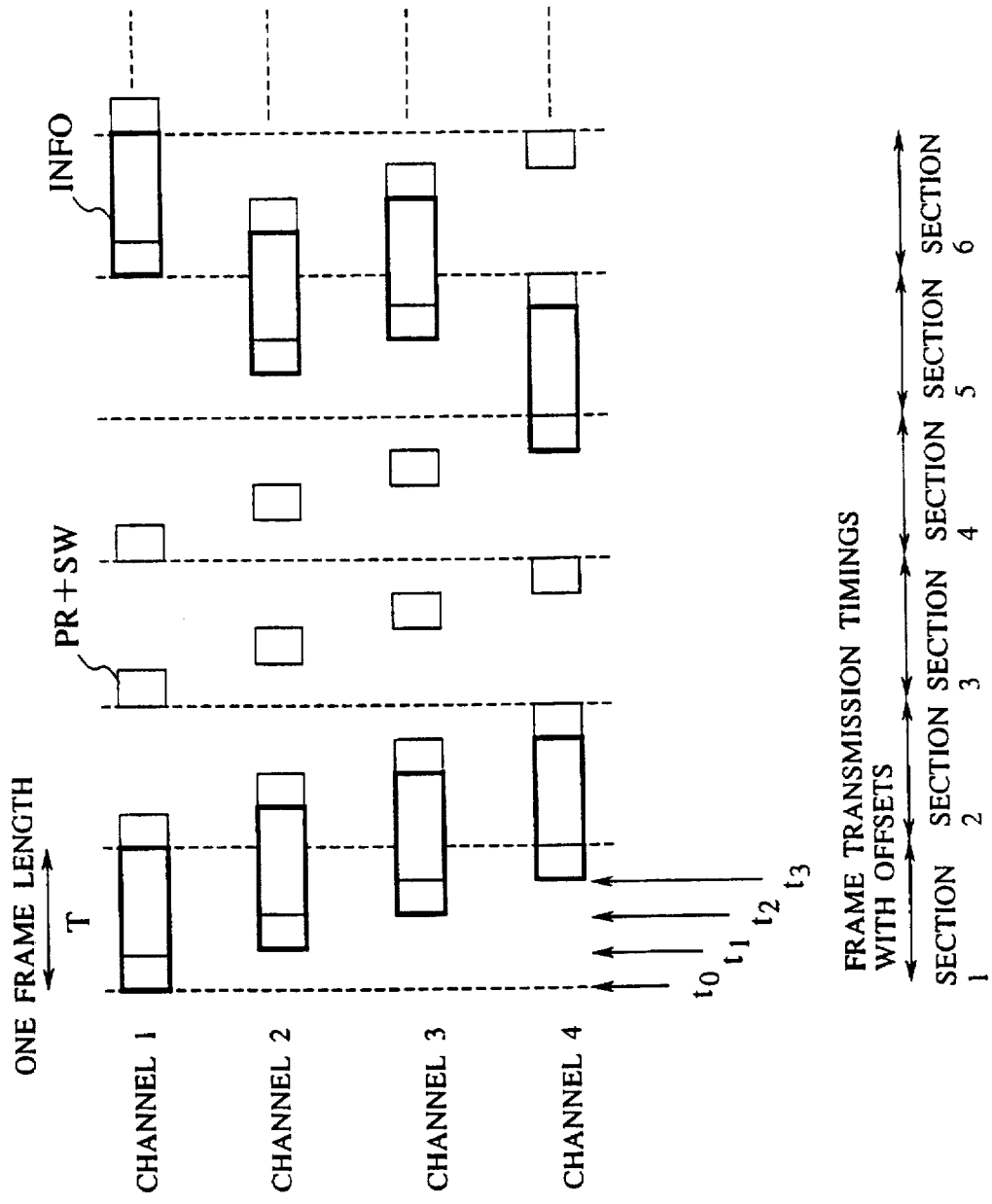
FIG. 31 is a timing chart showing a frame transmission state at a time of the VOX control of a plurality of channels in the fourth embodiment of the present invention.

FIG. 30 is showing a configuration of a base station transmission system for the CDMA mobile communication system in this fourth embodiment, where 401 is an antenna for irradiating an output of a transmission amplifier 402, 402 is a transmission amplifier for amplifying an output of a combiner 403 and sending it into the antenna 401, and 403 is a combiner for combining outputs of transmission ON/OFF control circuits 431 to 43n for respective channels together and sending it into the transmission amplifier 402. On the other hand, regarding the channel corresponding portion, each channel has the same configuration, so that only one sequence will be explained. 481 is an encoder circuit for encoding a data sequence and sending it out to a transmission data presence/absence judgment circuit 471, 471 is a transmission data presence/absence judgment circuit for judging speech/silence in a case of speeches or data presence/absence in a case of data for each frame in the encoded transmission data sequence, notifying it to the transmission ON/OFF control circuit 431 for each frame, and sending the encoded data signal into a modulation circuit 461, 461 is a modulation circuit for modulating the encoded data signal, 451 is a transmission timing adjustment circuit for adjusting a transmission timing by a timing in which a frame transmission reference timing from a reference timing generation circuit 409 is offset by as much time as specified from a control unit 410, 441 is a spreader for spreading an output of the transmission timing adjustment circuit 451, and 431 is a transmission ON/OFF control circuit for turning a transmission OFF for a data portion of a silence or no data frame, and turning it ON for the other portions according to signals from the transmission data presence/absence judgment circuit 471, among the signals from the transmission timing adjustment circuit 451 through the spreader 441. Also, 409 is a reference timing generation circuit for supplying the frame transmission reference timing to the transmission timing adjustment circuits 451 to 45n, 410 is a control unit for specifying timing offset amounts from the frame transmission reference timing for each channel to the transmission timing adjustment circuits 451 to 45n, and 411 is a spread code generation circuit for specifying the spread code to the spreaders 441 to 44n under the control of the control unit 410.

Next, a manner of determining an amount of offset to be set by the control unit 410 will be explained.

At the control unit 410, one frame is divided into a plurality of timings and these timings are set in correspondence to the offset amounts, and the timings, i.e., the offset amounts are randomly selected and set up at a time of the channel allocation. For example, FIG. 31 is an example in which four transmission timing offsets are set up with respect to the frame transmission reference timings of four channels. When the frame length is T, the offset amounts are $t_0=0$ (coinciding with the frame transmission reference timing), $t_1=T/4$, $t_2=T/2$, and $t_3=3T/4$. At the base station, at a time of allocating the radio channels, they are allocated by randomly selecting from these four timings. FIG. 31 is showing a situation in which four channels are allocated to be mutually different as an example. As a result, in the section 2 for example, four of PR+SW would have been overlapping conventionally such that a number of simultaneous communications cannot be increased even if the VOX control is carried out, but as the offsets are set on the transmission timings, PR+SW will not be overlapping, and a number of simultaneous communications can be increased and it is possible to take an advantage of the effect of the reduction of an amount of interference due to the VOX control. Also, as in the section 5, even when there is a frame for which the transmission is not turned OFF, the interference of the PR+SW portion is going to be reduced.

Next, regarding the unit of the offset width, it is preferable to make this to be about a length of a portion transmitted by a frame for which the data transmission is turned OFF (a length of PR+SW in this fourth embodiment). The reason is that if it has a length shorter than that, it is expected that the interference will be increased as the PR+SW overlaps partially, and also, if it has a length longer than that, it is expected that the lowering of the efficiency due to the appearance of the gaps will be caused.

Also, regarding the randomizing, it is also possible to use a method for selecting and setting the offset amounts at a time of the channel allocation such that numbers of mobile stations which are communicating at respective timings become as equal as possible.

Next, a case of upward (a signal transmission from a mobile station to a base station) will be explained.

Figure 32:
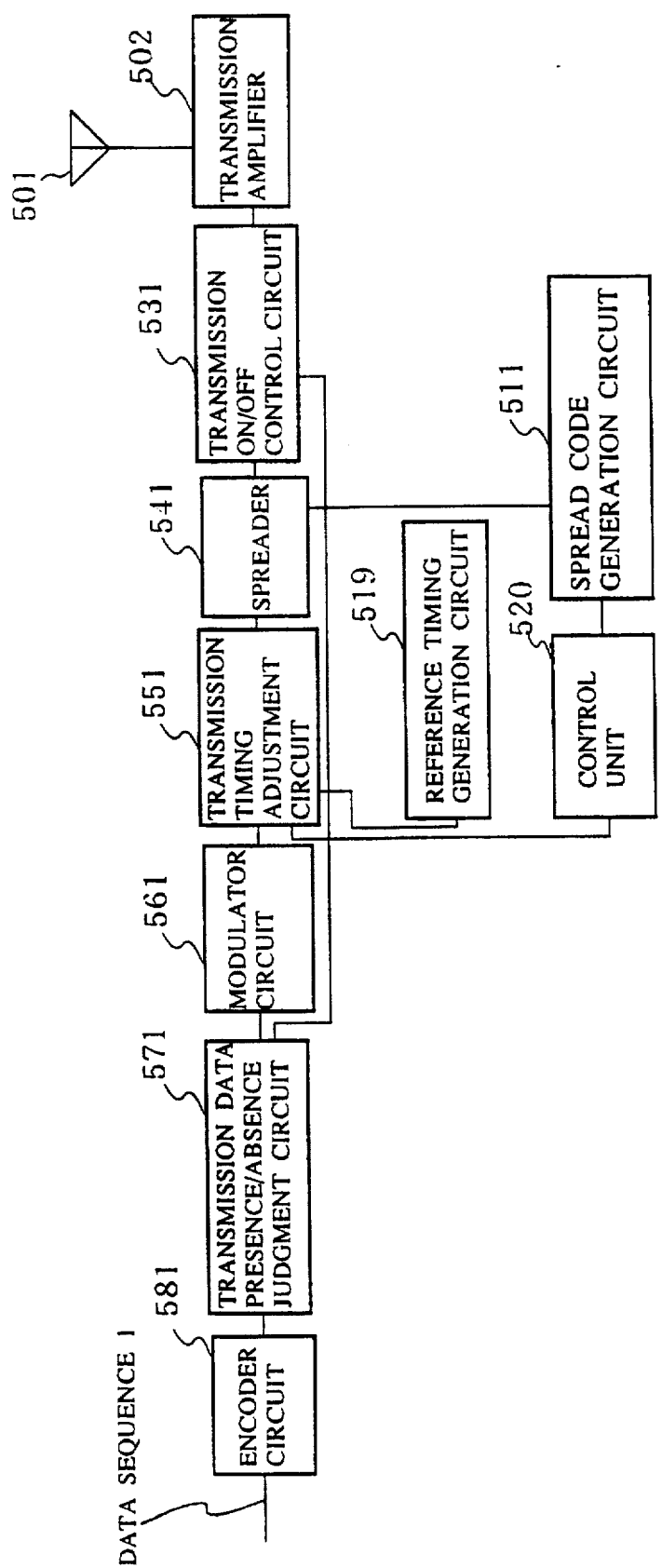
FIG. 32 is a block diagram showing a configuration of a mobile station in a CDMA mobile communication system according to the fourth embodiment of the present invention.

FIG. 32 is showing a configuration of a mobile station transmission system for the CDMA mobile communication system in this fourth embodiment, where 501 is an antenna for irradiating an output of a transmission amplifier 502, 502 is a transmission amplifier for amplifying an output of a transmission ON/OFF control circuit 531 and sending it into the antenna 501, 581 is an encoder circuit for encoding a data sequence and sending it out to a transmission data presence/absence judgment circuit 571, 571 is a transmission data presence/absence judgment circuit for judging speech/silence in a case of speeches or data presence/absence in a case of data for each frame in the encoded transmission data sequence, notifying it to the transmission ON/OFF control circuit 531 for each frame, and sending the encoded data signal into a modulation circuit 561, 561 is a modulation circuit for modulating the encoded data signal, 551 is a transmission timing adjustment circuit for adjusting a transmission timing by a timing in which a frame transmission reference timing from a reference timing generation circuit 509 is offset by as much time as specified from a control unit 520, 541 is a spreader for spreading an output of the transmission timing adjustment circuit 551, and 531 is a transmission ON/OFF control circuit for turning a transmission OFF for a data portion of a silence or no data frame, and turning it ON for the other portions according to signals from the transmission data presence/absence judgment circuit 571, among the signals from the transmission timing adjustment circuit 551 through the spreader 541. Also, 509 is a reference timing generation circuit for supplying the frame transmission reference timing to the transmission timing adjustment circuit 551, 520 is a control unit for specifying timing offset amounts from the frame transmission reference timing for each channel to the transmission timing adjustment circuit 551, and 511 is a spread code generation circuit for specifying the spread code to the spreader 541 under the control of the control unit 520.

At the mobile station, the frame reference timings are generated by the reference timing generation circuit 509 according to the signals from the base station. The frame reference timings from the base station themselves are randomized, so that by making the mobile station to transmit in synchronization with them, the similar effect as the downward can also be obtained for the upward. Also, in a case the base station transmissions are synchronized among the channels, it suffices to select random values and set one of them as the transmission timing offset amount at the control unit 520 of the mobile station. It may also be fine to select the offset amount of the mobile station at the base station and set it by notifying it to the mobile station.

As in the above, in this fourth embodiment, by setting an offset to the transmission timing randomly for each radio channel, the interference between the radio channels is reduced by making portions which are transmitting radio waves to be not overlapping as much as possible at a time of carrying out the VOX control, and the large channel capacity is secured by increasing the statistical multiplexing effect. Here, a scheme of this fourth embodiment has a particularly large effect in the CDMA scheme in which the radio channels can be the interference with each other as the radio channels are operated at the identical frequency.

Note that, in this fourth embodiment, the adjustment of the transmission timing is carried out before the modulated signal is entered into the spreader, in both the base station and the mobile station, so that it is possible to use a common long code in the identical phase at a time of transmission. By means of this, there is no need to have a plurality of long code generation circuits, and it becomes possible to operate it in the single phase within the device, so that there are advantages that the device configuration becomes simple while the phase data to be notified, etc., can be simplified.

Note that, in each embodiment described above, a case in which one base station supports one radio cell has been explained as an example, but it is also possible for one base station to support a plurality of radio cells (also called sectors). In such a case, the control channel and the communication channel are constructed for each radio cell supported by each base station, and the perch channel is also provided for each radio cell. Namely, it is going to have a configuration similar to a case in which the base station is provided for each radio cell. In this case, it suffices to use a number for uniquely identifying each cell (or sector) within the system instead of the base station identification number in each embodiment described above. For example, by using that in which the base station identification number and the cell (or sector) number within the base station are combined, it becomes possible to identify each cell (or sector) in the entire system. In this case, the Permuted BASE ID in the long code constituent elements for the downward control channel, the downward communication channel, and the upward control channel shown in FIG. 14 and FIG. 15 described above is going to be replaced by a Permuted (BASE ID+Cell ID). As for the upward communication channel, it suffices to be the same as in FIG. 16 described above.

We claim:

1. In a CDMA mobile communication system formed by a plurality of base stations and at least one mobile station which communicate in a CDMA scheme through radio channels, a CDMA mobile communication method comprising:

a step of selecting one of a plurality of prescribed short spread codes, and transmitting by spreading data sequence to be transmitted by using the selected short spread code and a prescribed long spread code with a code length longer than said short spread code, at either one station of each base station and the mobile station; and a step of receiving the data sequence from said either one station, and reproducing the data sequence before spreading by despreading the received data sequence by using said selected short spread code and said prescribed long spread code, at another one station of each base station and the mobile station;

wherein the radio channels for making a communication between said each base station and the mobile station comprises control/communication channels for communicating the data sequence which is spread by using said selected short spread code and said prescribed long spread code, and an additional channel containing a portion for notifying a phase information of a spread code by which said data sequence is spread which is for use in synchronization of channel spread code.

2. The CDMA mobile communication method as described in claim 1, wherein said prescribed long spread code is a spread code unique to the mobile station or a cell supported by each base station which is said either one station, and said plurality of prescribed short spread codes are spread codes common to cells supported by said plurality of base stations.

3. The CDMA mobile communication method as described in claim 1, wherein said prescribed long spread code is a bit sequence containing a bit pattern corresponding to an identification number of the mobile station or a cell supported by each base station which is said either one station.

4. The CDMA mobile communication method as described in claim 1, wherein said prescribed long spread code is generated by setting a bit pattern corresponding to an identification number of the mobile station or a cell supported by each base station which is said either one station into a shift register as an initial value, and shifting said initial value.

5. The CDMA mobile communication method as described in claim 1, wherein a total number of the prescribed long spread codes is greater than or equal to a total number of the mobile stations or cells utilized in said CDMA mobile communication system.

6. The CDMA mobile communication method as described in claim 1, wherein a total number of said plurality of prescribed short spread codes is greater than or equal to a total number of the radio channels within a cell supported by said each base station.

7. The CDMA mobile communication method as described in claim 1, wherein said either one station autonomously determines said prescribed long spread code, and autonomously selects and allocates said plurality of prescribed short spread codes such that a required transmission rate is satisfied and there is no overlap among the short spread codes within an identical cell.

8. The CDMA mobile communication method as described in claim 1, wherein said either one station spreads the data sequence to be transmitted by a spread code obtained by multiplying said selected short spread code and said prescribed long spread code, and said another one station despreads the received data sequence by a spread code obtained by multiplying said selected short spread code and said prescribed long spread code.

9. The CDMA mobile communication method as described in claim 1, wherein said either one station divides the data sequence to be transmitted into a plurality of sequences, and transmits a plurality of divided data sequences obtained by spreading the divided plurality of sequences by using mutually different ones of said plurality of prescribed short spread codes and said prescribed long spread code respectively, and said another one station despreads the received divided data sequences by using mutually different ones of said plurality of prescribed short spread codes and said prescribed long spread code, and reproduces the data sequence before spreading by composing the despread divided data sequences.

10. The CDMA mobile communication method as described in claim 1, wherein said additional channel is spread by using only said selected short spread code.

11. The CDMA mobile communication method as described in claim 1, wherein each base station which is said either one station transmits said phase information by said additional channel, and the mobile station which is said another one station establishes a channel synchronization by generating the spread code by which said data sequence is spread, according to said phase information received by said additional channel.

12. The CDMA mobile communication method as described in claim 1, wherein the data sequence to be communicated by downward control/communication channel and an upward control channel is spread by using a long spread code determined by data containing an identification number given to a cell supported by said each base station, and the data sequence to be communicated by an upward communication channel is spread by using a long spread code determined by data containing an identification number given to said mobile station.

13. The CDMA mobile communication method as described in claim 1, wherein said phase information indicates a phase of said prescribed long spread code which determines the spread code by which said data sequence is spread.

14. The CDMA mobile communication method as described in claim 1, wherein said phase information indicates a number of shifts for an initial value required in generating said prescribed long spread code at a shift register for generating said prescribed long spread code from a prescribed initial value.

15. The CDMA mobile communication method as described in claim 1, wherein in a case of carrying out a handover for said mobile station with said each base station as a handover source and another base station as a handover target, said mobile station obtains a phase relationship data for a phase of a long spread code for a transmission signal to be transmitted from the mobile station and said phase information received through said additional channel from said handover target, obtains a time relationship data for a timing corresponding to the phase relationship data and a timing of said transmission signal, and notifies the obtained phase relationship data and time relationship data to said handover target, while establishing a synchronization of control/communication channels transmitted from said handover target by generating a long spread code according to the phase relationship data, and said handover target establishes a synchronization of control/communication channels transmitted from said mobile station by generating a long spread code according to the phase relationship data and the time relationship data notified from said mobile station.

16. The CDMA mobile communication method as described in claim 1, wherein in a case of carrying out a handover for said mobile station with said each base station as a handover source and another base station as a handover target, said mobile station obtains a phase difference Ld between said phase information received by said additional channel from said handover target and a phase of a long spread code for a transmission signal to be transmitted from the mobile station, obtains a time difference Td between a timing corresponding to said phase information and a prescribed timing of said transmission signal, and notifies the obtained phase difference Ld and time difference Td to said handover target, while establishing a synchronization of control/communication channels transmitted from said handover target by generating a long spread code according to said phase information, and said handover target establishes a synchronization of control/communication channels transmitted from said mobile station by generating a long spread code according to the phase difference Ld and the time difference Td notified from said mobile station.

17. The CDMA mobile communication method as described in claim 1, wherein said mobile station determines whether or not to carry out a handover and a handover target according to a reception level of said additional channel from a base station other than a currently communicating base station.

18. In a CDMA mobile communication system formed by a plurality of base stations and at least one mobile station which communicate in a CDMA scheme through radio channels, a CDMA mobile communication method comprising:

a step of communicating by spreading each one of data to be communicated between a handover source base station and the mobile station and data to be communicated between a handover target base station and said mobile station by using both a long spread code and a short spread code;

a step of carrying out a handover by composing data received from the handover source base station and data received from the handover target base station by adjusting timings at said mobile station; and a step of carrying out a handover by composing data received from the mobile station at a cell of handover source and data received from the mobile station at a cell of handover target by adjusting timings at each base station or an upper level device connected to that base station.

19. The CDMA mobile communication method as described in claim 18, wherein at said step of communicating, downward data are spread by spread codes which are different among cells in the handover, and which are generated by combining a long spread code unique to a cell supported by each base station and one short spread code selected from a plurality of short spread codes which are common to cells supported by said plurality of base stations.

20. The CDMA mobile communication method as described in claim 18, wherein at said step of communicating, upward data are spread by a spread code which is identical among cells in the handover, and which is generated by combining a long spread code unique to said mobile station and one short spread code selected from a plurality of short spread codes which are common to cells supported by said plurality of base stations and identical among cells in the handover.

21. In a CDMA mobile communication system formed by a plurality of base stations and at least one mobile station which communicate in a CDMA scheme through radio channels, a CDMA mobile communication method comprising:

a step of controlling transmission frames to be transmitted through at least one radio channel such that a transmission of a data portion is not carried out for a frame without data to be transmitted, in at least one of each base station and the mobile station;

a step of randomly allocating an offset with respect to a transmission timing for each channel from a plurality of prescribed offset amounts; and a step of transmitting said transmission frames through each channel at a transmission timing with the offset allocated by said step of allocating.

22. The CDMA mobile communication method as described in claim 21, wherein said plurality of prescribed offset amounts are set up in units equal to a length of a portion other than a transmission target data in each transmission frame.

23. A CDMA mobile communication system formed by a plurality of base stations and at least one mobile station which communicate in a CDMA scheme through radio channels, in which:

either one station of each base station and the mobile station has means for selecting one of a plurality of prescribed short spread codes, and means for transmitting by spreading data sequence to be transmitted by using the selected short spread code and a prescribed long spread code with a code length longer than said short spread code; and another one station of each base station and the mobile station has means for receiving by reproducing the data sequence before spreading by despreading the data sequence from said either one station by using said selected short spread code and said prescribed long spread code;

wherein the radio channels for making a communication between said each base station and the mobile station comprises control/communication channels for communicating the data sequence which is spread by using said selected short spread code and said prescribed long spread code, and an additional channel containing a portion for notifying a phase information of a spread code by which said data sequence is spread which is for use in synchronization of channel spread code.

24. The CDMA mobile communication system as described in claim 23, wherein said prescribed long spread code is a spread code unique to the mobile station or a cell supported by each base station which is said either one station, and said plurality of prescribed short spread codes are spread codes common to cells supported by said plurality of base stations.

25. The CDMA mobile communication system as described in claim 23, wherein said prescribed long spread code is a bit sequence containing a bit pattern corresponding to an identification number of the mobile station or a cell supported by each base station which is said either one station.

26. The CDMA mobile communication system as described in claim 23, wherein said either one station has a shift register for generating said prescribed long spread code by setting a bit pattern corresponding to an identification number of the mobile station or a cell supported by each base station which is said either one station as an initial value, and shifting said initial value.

27. The CDMA mobile communication system as described in claim 23, wherein a total number of the prescribed long spread codes is greater than or equal to a total number of the mobile stations or cells utilized in said CDMA mobile communication system.

28. The CDMA mobile communication system as described in claim 23, wherein a total number of said plurality of prescribed short spread codes is greater than or equal to a total number of the radio channels within a cell supported by said each base station.

29. The CDMA mobile communication system as described in claim 23, wherein said either one station autonomously determines said prescribed long spread code, and autonomously selects and allocates said plurality of prescribed short spread codes such that a required transmission rate is satisfied and there is no overlap among the short spread codes within an identical cell.

30. The CDMA mobile communication system as described in claim 23, wherein said means for transmitting in said either one station spreads the data sequence to be transmitted by a spread code obtained by multiplying said selected short spread code and said prescribed long spread code, and said means for receiving in said another one station despreads the received data sequence by a spread code obtained by multiplying said selected short spread code and said prescribed long spread code.

31. The CDMA mobile communication system as described in claim 23, wherein said either one station divides the data sequence to be transmitted into a plurality of sequences, and transmits a plurality of divided data sequences obtained by spreading the divided plurality of sequences by using mutually different ones of said plurality of prescribed short spread codes and said prescribed long spread code respectively, and said another one station despreads the received divided data sequences by using mutually different ones of said plurality of prescribed short spread codes and said prescribed long spread code, and reproduces the data sequence before spreading by composing the despread divided data sequences.

32. The CDMA mobile communication system as described in claim 23, wherein said additional channel is spread by using only said selected short spread code.

33. The CDMA mobile communication system as described in claim 23, wherein each base station which is said either one station transmits said phase information by said additional channel, and the mobile station which is said another one station establishes a channel synchronization by generating the spread code by which said data sequence is spread, according to said phase information received by said additional channel.

34. The CDMA mobile communication system as described in claim 23, wherein said either one station spreads the data sequence to be communicated by downward control/communication channel and an upward control channel by using a long spread code determined by data containing an identification number given to a cell supported by said each base station, and spreads the data sequence to be communicated by an upward communication channel by using a long spread code determined by data containing an identification number given to said mobile station.

35. The CDMA mobile communication system as described in claim 23, wherein said phase information indicates a phase of said prescribed long spread code which determines the spread code by which said data sequence is spread.

36. The CDMA mobile communication system as described in claim 23, wherein said phase information indicates a number of shifts for an initial value required in generating said prescribed long spread code at a shift register for generating said prescribed long spread code from a prescribed initial value.

37. The CDMA mobile communication system as described in claim 23, wherein in a case of carrying out a handover for said mobile station with said each base station as a handover source and another base station as a handover target, said mobile station further has means for obtaining a phase relationship data for a phase of a long spread code for a transmission signal to be transmitted from said mobile station and said phase information received through said additional channel from said handover target, means for obtaining a time relationship data for a timing corresponding to the obtained phase relationship data and a timing of said transmission signal, and means for notifying the obtained phase relationship data and time relationship data to said handover target, and said mobile station establishes a synchronization of control/communication channels transmitted from said handover target by generating a long spread code according to the phase relationship data, while said handover target establishes a synchronization of control/communication channels transmitted from said mobile station by generating a long spread code according to the phase relationship data and the time relationship data notified from said mobile station.

38. The CDMA mobile communication system as described in claim 23, wherein in a case of carrying out a handover for said mobile station with said each base station as a handover source and another base station as a handover target, said mobile station further has means for obtaining a phase difference Ld between said phase information received by said additional channel from said handover target and a phase of a long spread code for a transmission signal to be transmitted from said mobile station, means for obtaining a time difference Td between a timing corresponding to said phase information and a prescribed timing of said transmission signal, and means for notifying the obtained phase difference Ld and time difference Td to said handover target, and said mobile station establishes a synchronization of control/communication channels transmitted from said handover target by generating a long spread code according to said phase information, while said handover target establishes a synchronization of control/communication channels transmitted from said mobile station by generating a long spread code according to the phase difference Ld and the time difference Td notified from said mobile station.

39. The CDMA mobile communication system as described in claim 23, wherein said mobile station further has means for determining whether or not to carry out a handover and a handover target according to a reception level of said additional channel from a base station other than a currently communicating base station.

40. A CDMA mobile communication system formed by a plurality of base stations and at least one mobile station which communicate in a CDMA scheme through radio channels, in which:

each base station and the mobile station have means for communicating by spreading each one of data to be communicated between a handover source base station and the mobile station and data to be communicated between a handover target base station and said mobile station by using both a long spread code and a short spread code;

said mobile station further has means for carrying out a handover by composing data received from the handover source base station and data received from the handover target base station by adjusting timings; and said each base station or an upper level device connected to that base station further has means for carrying out a handover by composing data received from the mobile station at a cell of handover source and data received from the mobile station at a cell of handover target by adjusting timings.

41. The CDMA mobile communication system as described in claim 40, wherein said means for communicating spreads downward data by spread codes which are different among cells in the handover, and which are generated by combining a long spread code unique to a cell supported by each base station and one short spread code selected from a plurality of short spread codes which are common to cells supported by said plurality of base stations.

42. The CDMA mobile communication system as described in claim 40, wherein said means for communicating spreads upward data by a spread code which is identical among cells in the handover, and which is generated by combining a long spread code unique to said mobile station and one short spread code selected from a plurality of short spread codes which are common to cells supported by said plurality of base stations and identical among cells in the handover.

43. A CDMA mobile communication system formed by a plurality of base stations and at least one mobile station which communicate in a CDMA scheme through radio channels, having:

means for controlling transmission frames to be transmitted through at least one radio channel such that a transmission of a data portion is not carried out for a frame without data to be transmitted, in at least one of each base station and the mobile station; and means for transmitting by randomly allocating an offset with respect to a transmission timing for each channel from a plurality of prescribed offset amounts.

44. The CDMA mobile communication system as described in claim 43, wherein said means for transmitting sets up said plurality of prescribed offset amounts in units equal to a length of a portion other than a transmission target data in each transmission frame.

* * * * *